(12) United States Patent
Vandenabeele et al.

(10) Patent No.: US 11,339,124 B2
(45) Date of Patent: May 24, 2022

(54) 3-(BENZYLAMINO)-4-(CYCLOHEXYL AMINO)-N-(2-(PIPERAZIN-1-YL)ETHYL) BENZENESULFONAMIDE DERIVATIVES AND RELATED FERROSTATIN-1 ANALOGUES AS CELL DEATH INHIBITORS FOR TREATING E.G. STROKE

(71) Applicants: VIB VZW, Ghent (BE); Universiteit Antwerpen, Antwerp (BE); Universiteit Gent, Ghent (BE)

(72) Inventors: Peter Vandenabeele, Sint-Amandsberg (BE); Tom Vanden Berghe, Haasdonk (BE); Koen Augustyns, Hoogstraten (BE); Sam Hofmans, Boom (BE); Pieter Van Der Veken, Sint-Katelijne-Waver (BE); Lars Devisscher, Turnhout (BE)

(73) Assignees: UNIVERSITEIT ANTWERPEN, Antwerp (BE); VIB VZW, Ghent (BE); UNIVERSITEIT GENT, Ghent (BE)

( * ) Notice: Subject to any disclaimer, the term of this patent is extended or adjusted under 35 U.S.C. 154(b) by 144 days.

(21) Appl. No.: 16/967,871

(22) PCT Filed: Feb. 5, 2019

(86) PCT No.: PCT/EP2019/052751
§ 371 (c)(1),
(2) Date: Aug. 6, 2020

(87) PCT Pub. No.: WO2019/154795
PCT Pub. Date: Aug. 15, 2019

(65) Prior Publication Data
US 2021/0094909 A1 Apr. 1, 2021

(30) Foreign Application Priority Data
Feb. 7, 2018 (GB) .................... 1801943

(51) Int. Cl.
| | | |
|---|---|---|
| *C07C 311/39* | (2006.01) | |
| *C07D 227/02* | (2006.01) | |
| *C07D 295/027* | (2006.01) | |
| *C07D 221/00* | (2006.01) | |
| *C07D 241/04* | (2006.01) | |
| *C07D 227/04* | (2006.01) | |

(52) U.S. Cl.
CPC .......... *C07C 311/39* (2013.01); *C07D 221/00* (2013.01); *C07D 227/02* (2013.01); *C07D 227/04* (2013.01); *C07D 241/04* (2013.01); *C07D 295/027* (2013.01)

(58) Field of Classification Search
CPC .. A61K 31/435; A61K 31/44; A61K 31/5375; A61K 31/4965; A61K 31/185; C07C 311/39; C07C 311/17; C07C 311/38; C07C 311/40; C07C 311/41; A61P 1/16; A61P 3/10; A61P 9/10; A61P 25/14; A61P 25/16; A61P 25/28; A61P 37/06; C07D 213/38; C07D 295/14; C07D 295/12; C07D 221/00; C07D 227/02; C07D 227/04; C07D 295/027; C07D 295/03; C07D 295/04; C07D 241/04
See application file for complete search history.

(56) References Cited

U.S. PATENT DOCUMENTS

2017/0313653 A1   11/2017   Vandenabeele et al.

FOREIGN PATENT DOCUMENTS

WO   2016075330 A1   5/2016

OTHER PUBLICATIONS

International Search Report dated Apr. 10, 2019 from PCT International Patent Appln. No. PCT/EP2019/052751.
Written Opinion dated Apr. 10, 2019 from PCT International Patent Appln. No. PCT/EP2019/052751.
Devisscher et al., "Discovery of Novel, Drug-Like Ferroptosis Inhibitors With in Vivo Efficacy," J. Med. Chem., vol. 61, No. 22, Oct. 25, 2018, pp. 10126-10140.

*Primary Examiner* — Robert H Havlin
(74) *Attorney, Agent, or Firm* — Amster, Rothstein & Ebenstein LLP

(57) ABSTRACT

The present invention relates to 3-(benzylamino)-4-(cyclohexylamino)-N-(2-(piperazin-1-yl)ethyl)benzenesulfonamide derivatives and related ferrostatin-1 (Fer-1) analogues as cell death inhibitors by inhibition of ferroptosis and/or oxytosis for the treatment of stroke, myocardial infarction, diabetes, sepsis, the prevention of transplant rejection, neurodegenerative diseases including Alzheimer's disease, Parkinson's disease, amyotrophic lateral sclerosis, multiple sclerosis, Huntington's disease, dementia with Lewy bodies and Friedreich's ataxia. The present invention further relates to pharmaceutical compositions of these compounds and discloses methods for making the compounds and the corresponding intermediate.

7 Claims, 7 Drawing Sheets

Figure 1:
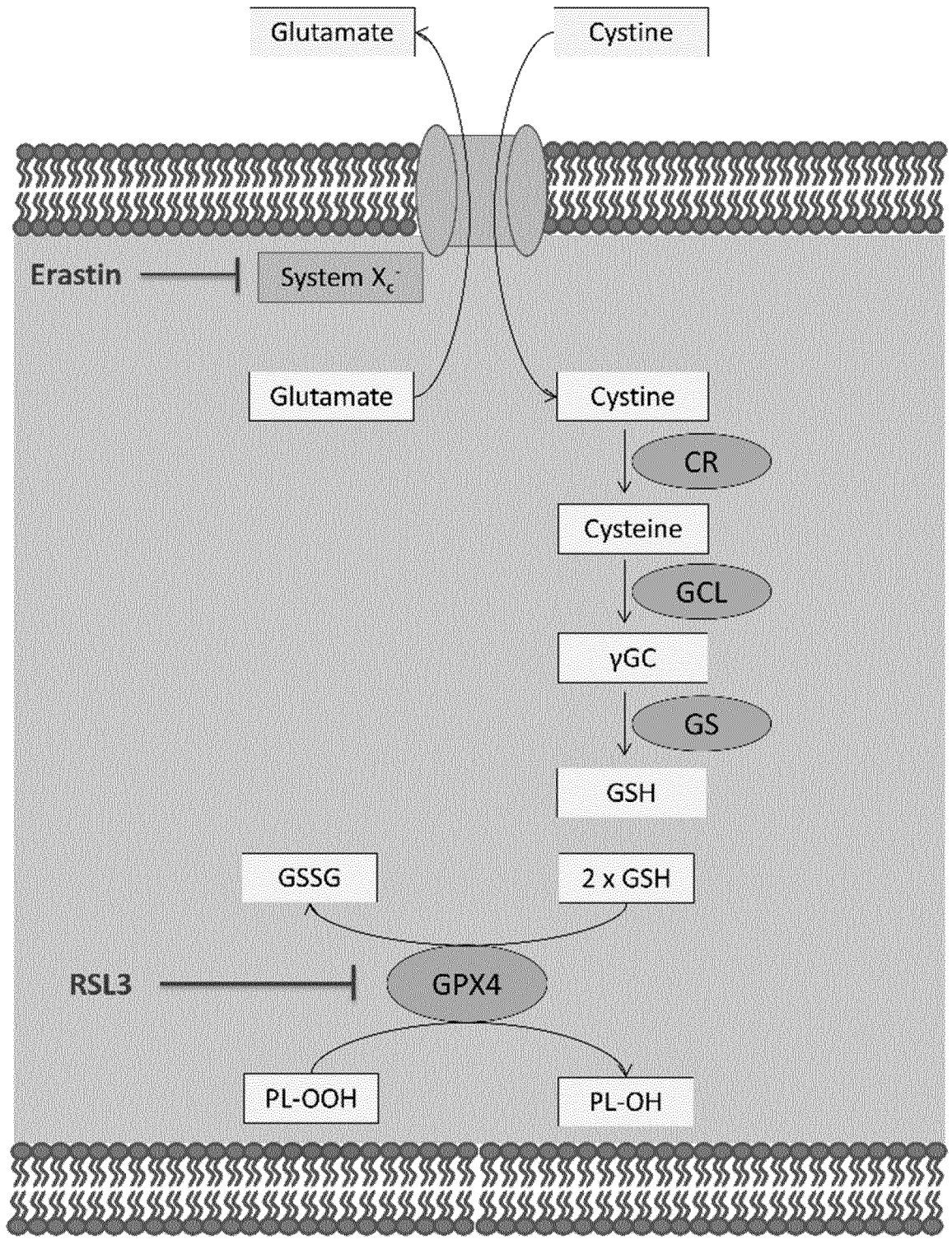

1
Ferrostatin-1

2
SRS11-92

3
SRS16-86

4
Sulfonamide analogue

Ferrostatin-1          Sulfonamide analogue          Novel inhibitors

A.

B.

3-(BENZYLAMINO)-4-(CYCLOHEXYLAMINO)-N-(2-(PIPERAZIN-1-YL)ETHYL) BENZENESULFONAMIDE DERIVATIVES AND RELATED FERROSTATIN-1 ANALOGUES AS CELL DEATH INHIBITORS FOR TREATING E.G. STROKE

CROSS-REFERENCE TO RELATED APPLICATIONS

This application is a U.S. national stage entry under 35 U.S.C. § 371 of PCT International Patent Application No. PCT/EP2019/052751, filed Feb. 5, 2019, which claims priority to GB Patent Application No. 1801943.0, filed Feb. 7, 2018, the contents of each of which are incorporated herein by reference in their entirety.

FIELD OF THE INVENTION

The present invention relates to the field of cell death, in particular regulated necrosis, more particularly iron dependent cell death. The invention provides compounds useful for inhibiting undesired cell death associated with diseases such as neurodegeneration and ischemia-reperfusion injury. The invention also provides compositions containing a pharmaceutically acceptable carrier and one or more compounds from the invention.

INTRODUCTION TO THE INVENTION

The classical notion that a cell can undergo cell death by either one of two distinct pathways, apoptosis or necrosis respectively, has been placed under scrutiny in recent years.[1] While apoptosis was always considered to be carried out following a strict mechanism involving cellular proteases called caspases, the execution of necrosis on the other hand was historically deemed to be fairly irregular.[2] The finding that tumor necrosis factor (TNF) can trigger various cell lines to undergo a form of regulated cell death with distinctively necrotic features resulted in an increased scientific interest towards regulated necrosis, of which the most studied form is RIPK-M LKL-mediated necroptosis.[3,4] So far a whole variety of different forms of regulated necrosis with each their distinctive pathways and effector molecules have been studied.[5,6] One molecule that is able to induce a form of regulated necrosis is erastin.[7] It was first proposed that erastin interacts with mitochondrial voltage-dependent anion channels (VDACs) which resulted in a RAS-RAF-MEK-dependent form of cell death due to the formation of reactive oxidative species (ROS).[8] However it was subsequently demonstrated by Dixon et al. that erastin induced a unique form of non-apoptotic cell death due to the inhibition of the membrane-bound cystine/glutamate antiporter System $X_c^-$.[9] This novel form of cell death was dubbed ferroptosis, which is characterized by iron-dependent accumulation of lipid hydroperoxides that disrupt membrane integrity leading to cell death. Ferroptosis may thus play a key role in the pathogenesis of degenerative diseases in which lipid peroxidation has been implicated. Interestingly, the execution of this form of cell death could be inhibited by the small molecule ferrostatin-1 (Fer-1, 1).[9] Even though target identification of Fer-1 remains a challenge, the mechanism of action of Fer-1 was recently proposed to derive from its reactivity as a radical-trapping antioxidant.[10] The molecular pathway of ferroptosis however, has been elucidated in recent years. Erastin, the most well-known inducer of ferroptosis, inhibits the membrane-bound cystine/glutamate antiporter System $X_c^-$, which allowed it to be classified as a class I ferroptosis inducer. (FIN) Blockage of this antiporter impairs the cellular uptake of cystine, an essential precursor in the synthesis of the cellular antioxidant glutathione (GSH). The resulting intracellular deficit of GSH in turn triggers the accumulation of ROS which causes cells to die by excessive oxidation of the membrane lipids. (FIG. 1)[11] In addition to class I FINs, ferroptosis can also be induced by molecules that directly target and inactivate gluthathione peroxidase 4 (GPX4) and are classified as class II FINs.[12,13] Seiler et al. showed that GPX4, a specific type of GSH-dependent selenoprotein, holds an essential role in the antioxidant network of the membranes of a cell. Inducible GPX4-KO significantly caused cell death due to excessive lipid peroxidation, a hallmark feature of ferroptosis.[14] GPX4 has the ability to reduce organic hydroperoxides to the corresponding alcohols while consuming GSH as a reducing agent, further implying the importance of intracellular GSH levels in ferroptosis.[15] Inactivation of GPX4 either directly or indirectly resulted in the accumulation of ROS followed by lipid membrane oxidation which disrupted cell membrane integrity. These findings further solidified GPX4 as a crucial protective enzyme that suppresses ferroptosis and it underlines the importance of the GSH-GPX4-axis considering redox homeostasis within the cell membrane (see FIG. 1). The clinical relevance of ferroptosis has been implied in various pathological settings.[17] Dixon et al. first showed that Fer-1 was able to prevent glutamate-induced neurotoxicity in a model that mimics the trauma a brain might undergo after a stroke or during neurodegenerative disease.[11] Another study in particular showed that ferroptosis might contribute in a whole array of diseases by showing that inhibition of ferroptosis significantly ameliorated the clinical outcome in models for Huntington's disease, periventricular leukomalacia and kidney dysfunction.[18] Since then multiple studies have implicated an important role of ferroptosis in various pathological conditions like ischemia-reperfusion injury[19], neuronal dysfunction[20], Alzheimer's disease[21], hair follicle morphogenesis[22], blood coagulation[23] and in the maturation of photoreceptor cells.[24] The design of novel and improved ferroptosis inhibitors is thus an interesting field of research. Fer-1 as an academic tool compound itself has some unfortunate shortcomings. The presence of a labile ester moiety results in the rapid hydrolysis of Fer-1 into its inactive carboxylic acid. Multiple attempts have been made to improve the potency of this type of molecule while also improving pharmacokinetic parameters of Fer-1. (2 and 3, FIG. 2)[18,25] While Skouta et al. thoroughly explored the structure-activity relationship (SAR) of the Fer-1 scaffold, we previously reported that the replacement of the labile ester moiety of Fer-1 by a more stable sulfonamide group yielded promising results. (4, see FIG. 2) This intervention significantly improved the metabolic stability while maintaining and even improving potency in a cell-based assay for ferroptosis. Several of these molecules however display a poorly soluble character[16] and WO2016/075330.

In the present invention we report the synthesis of a novel generation of ferroptosis inhibitors with improved ADME properties, an increased solubility and at the same time having a high cellular activity. The most potent molecules were selected and their pharmacokinetic properties were characterized in both in vitro and in vivo settings.

FIGURE LEGENDS

FIG. 1: The different relationships between System $X_c^-$, glutathione (GSH) synthesis, GPX4 and lipid peroxidation.

System $X_c^-$ facilitates the cellular uptake of cystine which is an important precursor in GSH synthesis. Cystine is reduced by cystine reductase (CR) to cysteine. Glutamate cysteine ligase (GCL) attaches a glutamate molecule to cysteine in order to generate γ-glutamyl cysteine (γGC). Addition of a glycine molecule by glutathione synthase (GS) results in the formation of a new molecule of GSH. GSH servers as an important reducing cofactor for GPX4 by catalysing the reduction of lipid peroxides to their corresponding alcohols while also forming glutathione disulfide (GSSG). Erastin inhibits the cellular uptake of cystine and thus impairs intracellular synthesis of GSH. Depletion of GSH leads to the indirect inactivation of GPX4 and the resulting accumulation of lipid peroxides disrupts membrane integrity resulting in ferroptosis. RSL3 on the other hand acts directly by inactivating GPX4 and does not interfere with the cellular uptake of cystine or intracellular GSH synthesis. [6,16]

Figure 2:
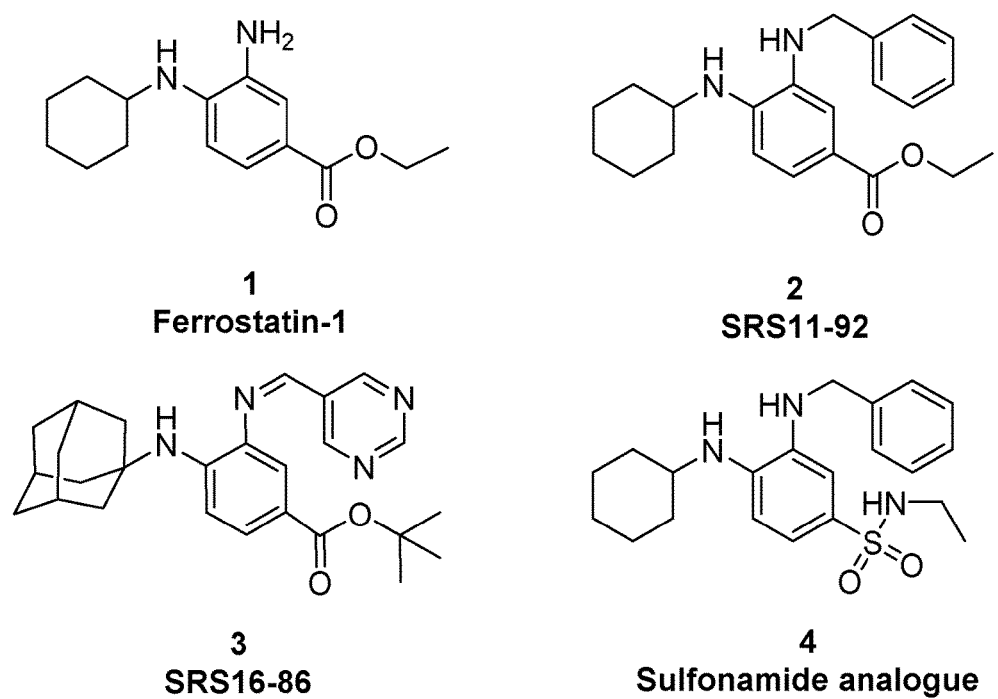

FIG. 2: The chemical structure of Ferrostatin-1 and other reported analogues.

Figure 3:
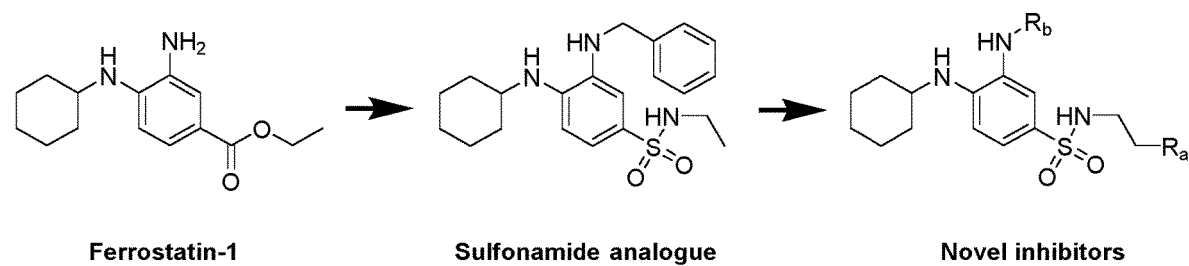

FIG. 3: Structural comparison of Ferrostatin-1 (Fer-1), our previously reported sulfonamide analogue of Fer-1 and the newly synthesized series.

Figure 4:
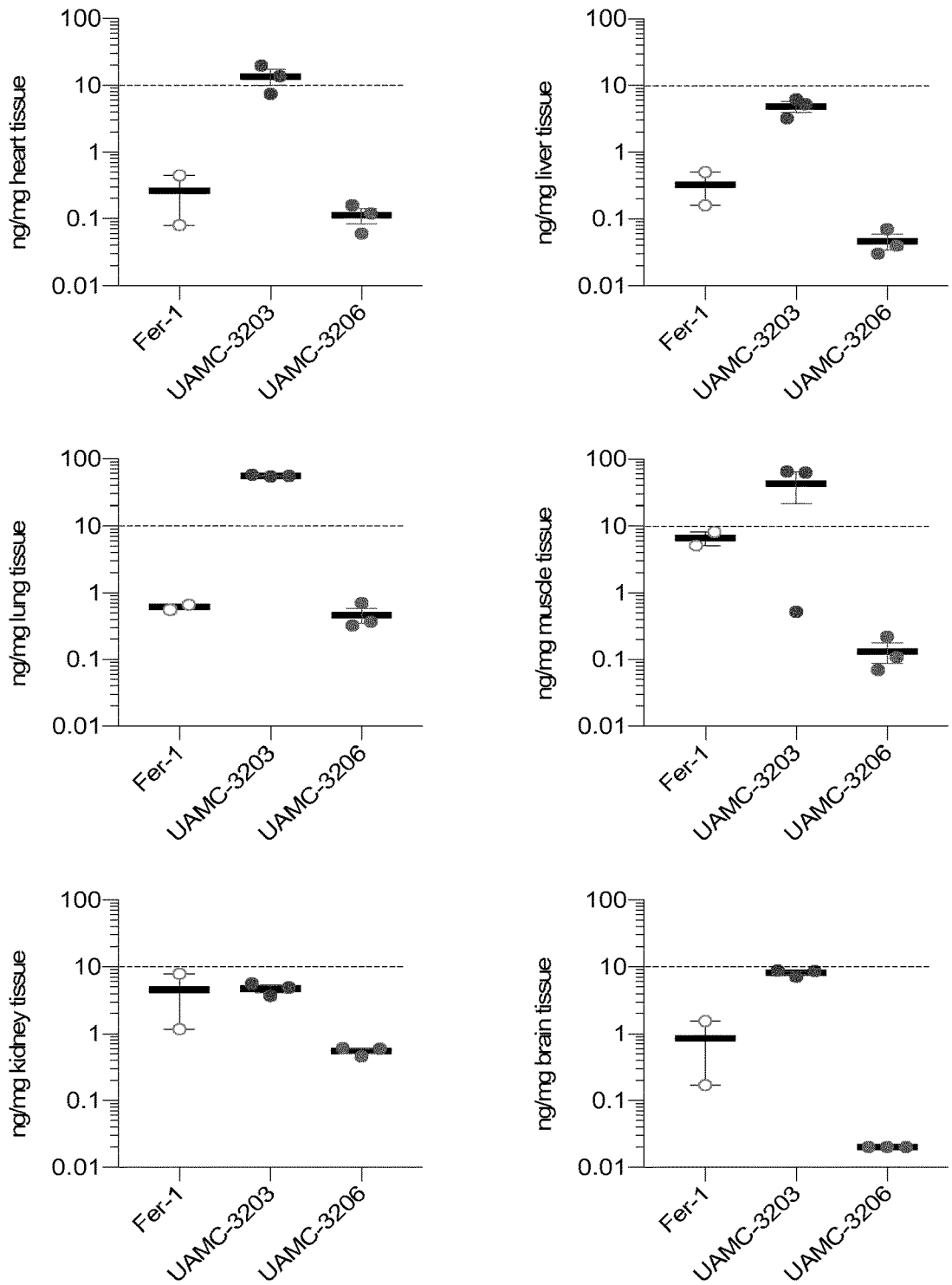
Figure 4:
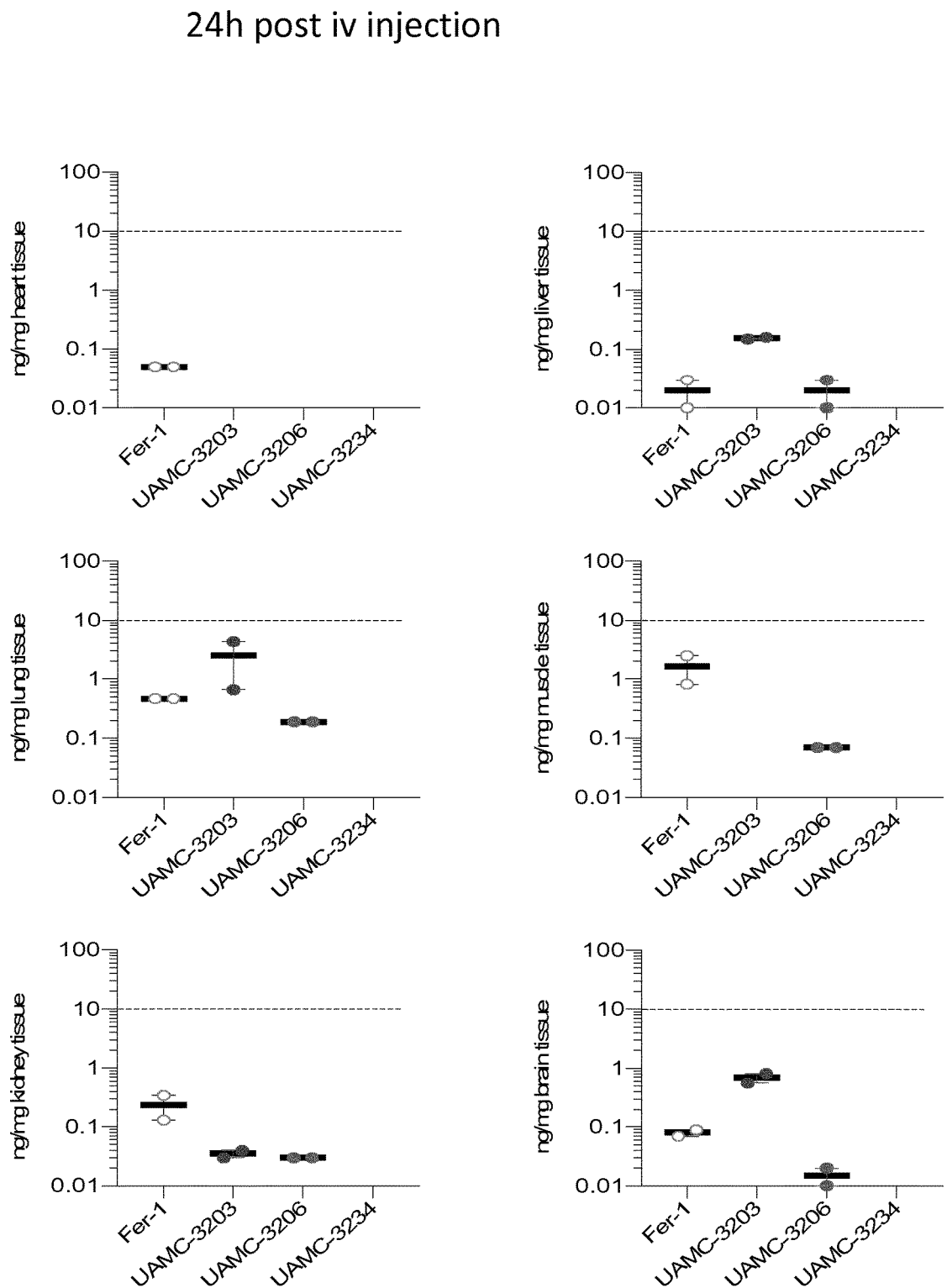

FIG. 4: Tissue distribution of ferrostatin-analogues. Equimolar amounts of Ferrostatin (Fer-1), compound 39 (depicted as UAMC-3203) and compound 38 (depicted as UAMC-3206) (~10 mg/kg) were injected intravenously 2 h (left panel) or 24 h (right panel) before tissue collection (heart, liver, lung, muscle, kidney and brain). Tissues were collected, snap frozen in liquid nitrogen, homogenized and stored at −80° C. until analysis. The tissue samples for LC-MS were further processed by protein precipitation by diluting 20 µL of the homogenate with 80 µL ACN containing IS (tolbutamide). After centrifugation, the supernatant was further diluted in the appropriate solvent.

Figure 5:
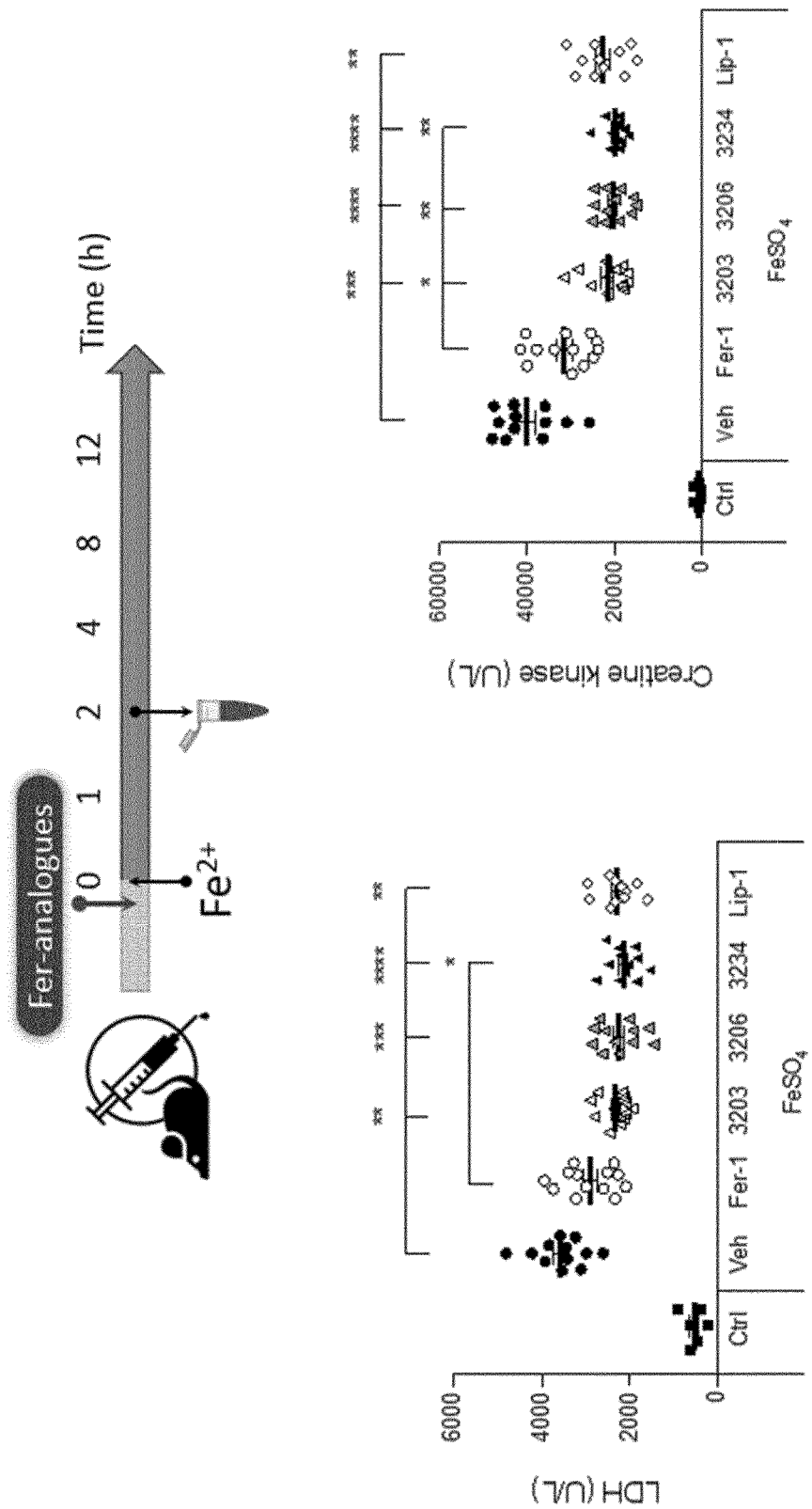
Figure 5:
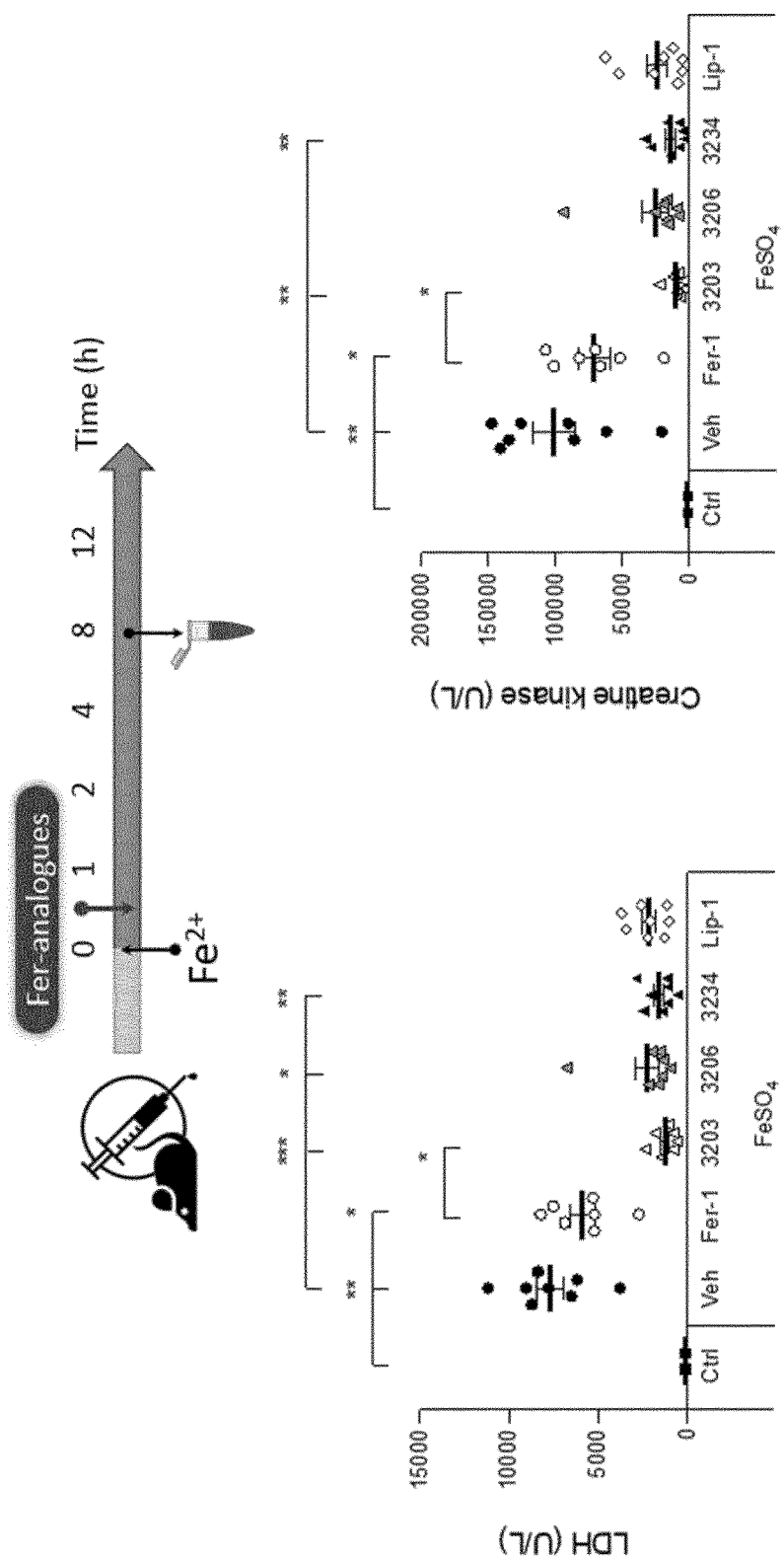

FIG. 5: A. Ferrostatin-analogues protect against acute iron poisoning induced organ damage, while benchmark Fer-1 does not show any significant protection. Equimolar amounts of ferroptosis inhibitors (~10 mg/kg) were injected iv 15 min before ip injection of $FeSO_4$ (300 mg/kg). Plasma was collected 2 h after $FeSO_4$-challenge and analyzed for the presence of lactate dehydrogenase (LDH) and creatine kinase. Fer-1 is ferrostatin, 3234 is compound 37,3206 is compound 38 and 3203 is compound 39 (see Table 1 for numbering and structure). B. Ferrostatin-analogues strongly protect against acute iron poisoning induced organ damage in a therapeutic setting, while benchmark Fer-1 only shows minor protection. Equimolar amounts of ferroptosis inhibitors (~10 mg/kg) were injected iv 30 min after ip injection of $FeSO_4$ (300 mg/kg). Plasma was collected 8 h after $FeSO_4$-challenge and analyzed for the presence of lactate dehydrogenase (LDH) and creatine kinase.

Figure 6:
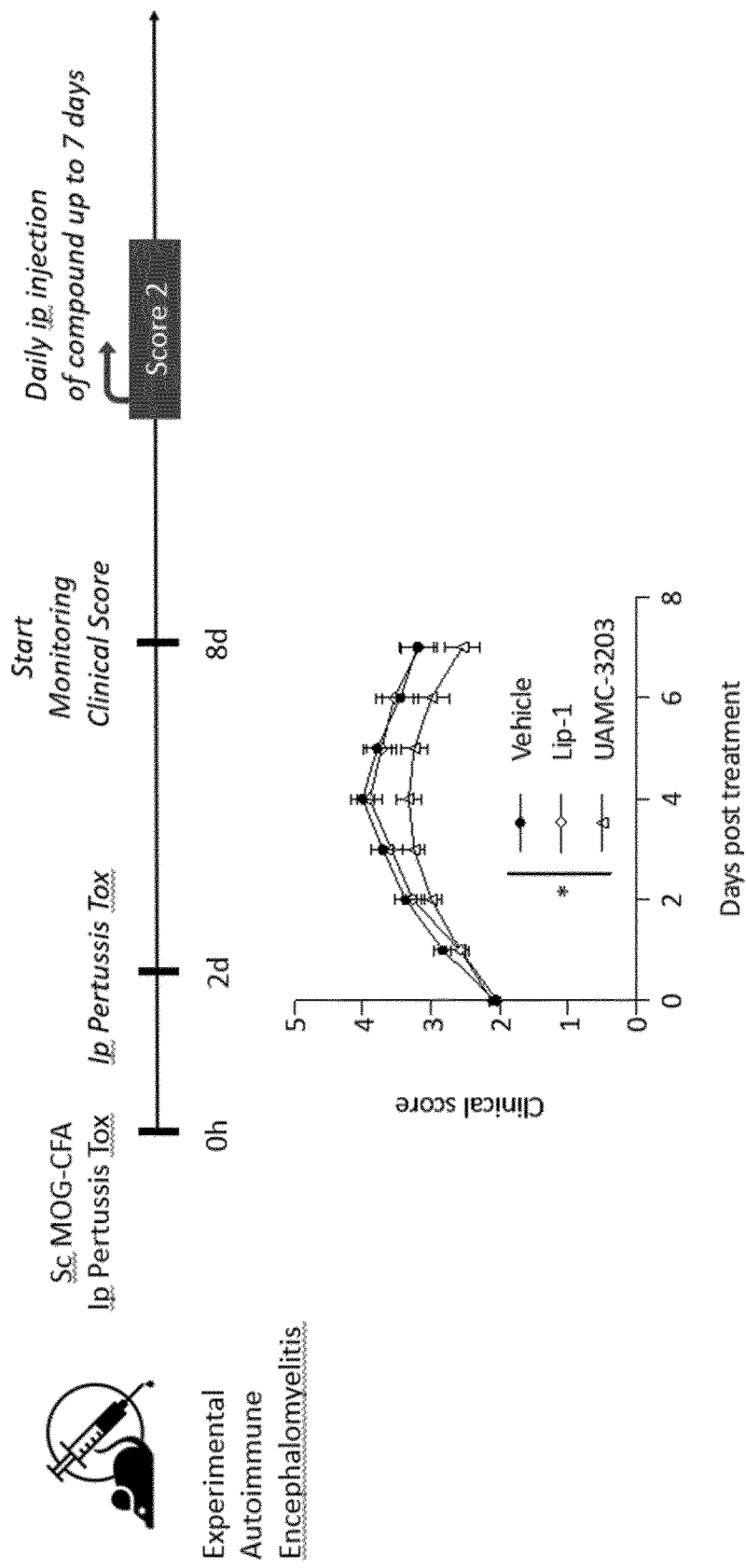

FIG. 6: Therapeutic intervention with compound 39 (depicted as UAMC-3203) ameliorates clinical signs in an experimental autoimmune encephalomyelitis model. 9-10-week-old C57BL/6N male mice were immunized subcutaneously with an emulsion of (MOG) 35-55 peptide (10 mg/kg) and CFA supplemented with *Mycobacterium tuberculosis* H37RA (50 mg/kg). The mice received an intraperitoneal injection of pertussis toxin (5 ug/kg) at the time of immunization and 48 h later. In a therapeutic procedure, mice that reached the clinical sore of 2 were injected intraperitoneally every day with equimolar amounts of Fer-1, compound 39, Liproxtatin-1 or vehicle (~1-mg/kg) and were scored daily. Clinical signs of disease were scored on a scale of 0 to 6, as follows: 0, normal; 1, weakness of tail; 2, complete loss of tail tonicity; 3, partial hind limb paralysis; 4, complete hind limb paralysis; 5, forelimb paralysis or moribund; and 6, death (McGuire C et al (2013) *J. Immunol.* 190(6): 2896).

DETAILED DESCRIPTION OF THE INVENTION

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. Unless specifically defined herein, all terms used herein have the same meaning as they would to one skilled in the art of the present invention. The definitions provided herein should not be construed to have a scope less than understood by a person of ordinary skill in the art.

In one embodiment the invention provides a compound depicted in formula (I)

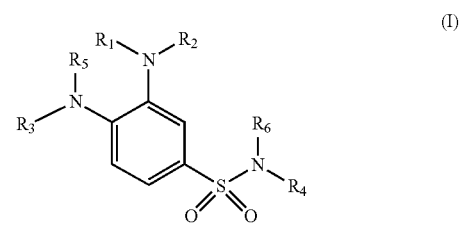

(I)

wherein

R1 is selected from the groups consisting of H and C1-C4-alkyl aryl;

R2 is C1-C4-alkyl aryl;

R3 is selected from the groups consisting of a C3-C12-cycloalkyl optionally substituted with one of more halogens, optionally replacing one or more carbons by heteroatoms in the cycloalkyl ring structure;

R4 is selected from the groups consisting C1-C4-alkyl, wherein said C1-C4 alkyl is terminated with an R7 group wherein R7 is a C3-C10-heterocycle optionally substituted with one or more halogens, optionally replacing one or more carbons by heteroatoms in the heterocyclic ring structure.

R5 is selected from the groups consisting H or C3-C12-cycloalkyl optionally substituted with one of more halogens, optionally replacing one or more carbons by heteroatoms in the cycloalkyl ring structure;

R6 is selected from the groups consisting of H or a structure as defined in R4.

and pharmaceutically acceptable salts thereof, and individual enantiomers and diastereomers thereof.

In yet another embodiment the invention provides a compound depicted in formula (I)

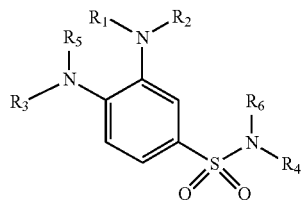

(I)

wherein
R1 is H;
R2 is C1-C4-alkyl aryl;
R3 is selected from the groups consisting of a C4-C8-cycloalkyl optionally substituted with one of more halogens, optionally replacing one or more carbons by heteroatoms in the cycloalkyl ring structure;
R4 is selected from the groups consisting C1-C4-alkyl, wherein said C1-C4 alkyl is terminated with an R7 group wherein R7 is a C4-C8-heterocycle optionally substituted with one or more halogens, optionally replacing one or more carbons by heteroatoms in the heterocyclic ring structure.
R5 is selected from the groups consisting H or C4-C8-cycloalkyl optionally substituted with one of more halogens, optionally replacing one or more carbons by heteroatoms in the cycloalkyl ring structure;
R6 is selected from the groups consisting of H or a structure as defined in R4.

In yet another embodiment the invention provides a compound depicted in formula (I)

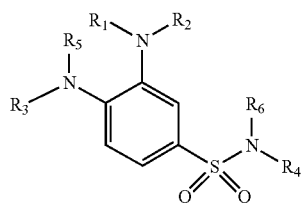

(I)

wherein
R1 is H;
R2 is C1-C4-alkyl aryl;
R3 is selected from the groups consisting of a C6-cycloalkyl optionally substituted with one of more halogens, optionally replacing one or more carbons by heteroatoms in the cycloalkyl ring structure;
R4 is selected from the groups consisting C1-C4-alkyl, wherein said C1-C4 alkyl is terminated with an R7 group wherein R7 is a C6-heterocycle optionally substituted with one or more halogens, optionally replacing one or more carbons by heteroatoms in the heterocyclic ring structure.
R5 is selected from the groups consisting H or C6-cycloalkyl optionally substituted with one of more halogens, optionally replacing one or more carbons by heteroatoms in the cycloalkyl ring structure;
R6 is selected from the groups consisting of H or a structure as defined in R4.

and pharmaceutically acceptable salts thereof, and individual enantiomers and diastereomers thereof.

In yet another embodiment the invention provides a compound selected from the list consisting of 3-(benzylamino)-4-(cyclohexylamino)-N-(2-morpholinoethyl)benzenesulfonamide and 3-(benzylamino)-4-(cyclohexylamino)-N-(2-(piperazin-1-yl)ethyl)benzenesulfonamide hydrochloride.

Any of the compounds according to the invention can exist as one or more stereoisomers depending on the number of stereogenic centers (as defined by the IUPAC rules) in the compound. The invention thus relates equally to all the stereoisomers, and to the mixtures of all the possible stereoisomers, in all proportions. Typically one of the stereoisomers has enhanced biological activity compared to the other possibilities. The stereoisomers can be separated according to the methods that are known per se by the man ordinary skilled in the art. Similarly, where there are disubstituted alkenes, these may be present in E or Z form or as mixtures of both in any proportion. Furthermore it should be appreciated that all tautomeric forms (single tautomer or mixtures thereof), and racemic mixtures of compounds of formula (I) are included within the scope of the present invention.

The present invention also includes salts that the compounds of formula (I) may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium. The corresponding trimethylsulfonium salt may also be used.

The term "C1-C4-alkyl" refers to a linear or branched-chain saturated hydrocarbyl substituent (i.e., a substituent obtained from a hydrocarbon by removal of a hydrogen) containing one (1), two (2), three (3) or four (4) carbon atoms. Examples of such saturated substituents include methyl, ethyl, propyl (including n-propyl and isopropyl) and butyl (including n-butyl, isobutyl, sec-butyl and tert-butyl).

The terms "C3-C12 cycloalkyl", "C4-C8 cycloalkyl", and "C6-cycloalkyl" as used herein, refers to the radical of saturated aliphatic groups having a ring structure. Certain cycloalkyls have from 3-12 carbon groups in their ring structure, including 3, 4, 5, 6, 7, 8, 9, 10, 11 or 12 carbons in the ring structure or have from 4-8 carbon groups or 6 carbon groups in their ring structure. A preferred cycloalkyl structure is the C6 structure. Cycloalkyls can be further substituted with one or more halogens. Carbon atoms present in the C3-C12 cycloalkyls can be optionally replaced by one or more heteroatoms in the ring structure, particularly preferred heteroatoms are N, O and S.

The term "aryl" as used herein includes substituted or unsubstituted single-ring aromatic groups in which each atom of the ring is carbon, or nitrogen (if ring carbons are substituted). Preferably the ring is a 3- to 8-membered ring, more preferably a 6-membered ring. Aryl groups include benzene, naphthalene, phenol, aniline and the like.

The term "halogen" includes chloro, fluoro, bromo and iodo. Preferred halogens are chloro and fluoro.

The term "heteroatom" refers to any atom that is not carbon in a structure, oxygen (O), nitrogen (N), sulfur (S) or phosphor (P) are preferred heteroatoms, most preferred heteroatoms are N, S or O. In the present invention a heteroatom is used in the context of the replacement of a carbon (C) atom for a heteroatom in the backbone of a molecular structure such as for example a carbon which is replaced in N or O in a C1-C4 alkyl or in a C3-C12 cycloalkyl.

The term "substituent" refers to an atom, for example a halogen, or group of atoms substituted in place of a hydrogen atom on the chain of a hydrocarbon.

If substituents are described as being "independently selected" from a group, each substituent is selected independent of the other. Each substituent therefore may be identical to or different from the other substituent(s).

When an asymmetric center is present in a compound of formula (I) hereinafter referred to as a "compound of the invention," the compound may exist in the form of optical isomers (enantiomers). In one embodiment, the present invention comprises enantiomers and mixtures, including racemic mixtures of the compounds of formula I. In another embodiment, for compounds of formula I that contain more than one asymmetric center, the present invention comprises diastereomeric forms (individual diastereomers and mixtures thereof) of compounds. When a compound of formula I contains an alkenyl group or moiety, geometric isomers may arise.

The present invention comprises the tautomeric forms of compounds of formula I. Where structural isomers are interconvertible via a low energy barrier, tautomeric isomerism ('tautomerism') can occur. This can take the form of proton tautomerism in compounds of formula I containing, for example, an imino, keto, or oxime group, or so-called valence tautomerism in compounds which contain an aromatic moiety. It follows that a single compound may exhibit more than one type of isomerism. The various ratios of the tautomers in solid and liquid form are dependent on the various substituents on the molecule as well as the particular crystallization technique used to isolate a compound.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts. In one embodiment, hemisalts of acids and bases may also be formed, for example, hemisulphate and hemicalcium salts.

The present invention also includes isotopically labelled compounds, which are identical to those recited in formula I, but for the fact that one or more atoms are replaced by an atom having an atomic mass or mass number different from the atomic mass or mass number usually found in nature. Examples of isotopes that may be incorporated into compounds of the present invention include isotopes of hydrogen, carbon, nitrogen, oxygen, phosphorous, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention and pharmaceutically acceptable salts of said compounds or which contain the aforementioned isotopes and/or other isotopes of other atoms are within the scope of this invention. Certain isotopically labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, may afford certain therapeutic advantages resulting from greater metabolic stability, for example increased in vivo half-life or reduced dosage requirements and, hence, may be preferred in some circumstances, Isotopically labelled compounds of formula I of this invention may generally be prepared by carrying out the procedures disclosed in the Schemes and/or in the Examples and Preparations below, by substituting a readily available isotopically labelled reagent for a non-isotopically labelled reagent.

This invention also relates to pharmaceutical compositions containing one or more compounds of the present invention. These compositions can be utilized to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, intrathecally, intracerebroventricularly, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin. Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents. The compounds of this invention may also be administered parenterally, that is, subcutaneously, intravenously, intraocularly, intrasynovially, intramuscularly, or intraperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quaternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived from a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see for example U.S. Pat. No. 5,023,252). Such patches may be constructed for continuous, pulsatile, or on demand delivery of pharmaceutical agents. Controlled release formulations for parenteral administration include liposomal, polymeric microsphere and polymeric gel formulations that are known in the art. It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51 (4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid); alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine); adsorbents (examples include but are not limited to powdered cellulose and activated charcoal); aerosol propellents (examples include but are not limited to carbon dioxide, $CCl_2F_2$, $F_2ClC$—$CClF_2$ and $CClF_3$) air displacement agents (examples include but are not limited to nitrogen and argon); antifungal preservatives (examples include but are not limited to benzoic acid, butylparaben, ethylparaben, methylparaben, propylparaben, sodium benzoate); antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal); antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite); binding materials (examples include but are not limited to block polymers, natural and synthetic rubber, polyacrylates, polyurethanes, silicones, polysiloxanes and styrene-butadiene copolymers); buffering agents (examples include but are not limited to potassium metaphosphate, dipotassium phosphate, sodium acetate, sodium citrate anhydrous and sodium citrate dihydrate) carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection) chelating agents (examples include but are not limited to edetate disodium and edetic acid) colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate);

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures);

surfactants (examples include but are not limited to benzalkonium chloride, nonoxynol 10, oxtoxynol 9, polysorbate 80, sodium lauryl sulfate and sorbitan monopalmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, crosslinked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A between 0.01-5 mg/mL solution of the desired compound of this invention can be made using sterile, injectable water, and the pH is adjusted if necessary. The solution is diluted for administration to 0.02-2 mg/mL with sterile 5% dextrose and is administered as an IV infusion over about 60 minutes.

Lyophilised powder for IV administration: A sterile preparation can be prepared with (i) 1-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

0.01-5 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A large number of unit capsules are prepared by filling standard two-piece hard galantine capsules each with 1-100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 1-100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 1-100 mg of active ingredient, 0.2 mg of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Therapeutic Uses of the Compounds of the Invention

In another particular embodiment the invention provides the compounds of the invention or a pharmaceutical composition comprising one or more compounds of the invention for the inhibition of ferroptosis.

In another particular embodiment the invention provides the compounds of the invention or a pharmaceutical composition comprising one or more compounds of the invention for the inhibition of oxytosis.

In another particular embodiment the invention provides the compounds of the invention or a pharmaceutical composition comprising one or more compounds of the invention for the inhibition of oxytosis and ferroptosis.

In another particular embodiment the invention provides the compounds of the invention or a pharmaceutical composition comprising one or more compounds of the invention for the treatment of a mammal suffering from excessive ferroptosis in one or more organs.

In another particular embodiment the invention provides the compounds of the invention or a pharmaceutical composition comprising one or more compounds of the invention for the treatment of a mammal suffering from excessive oxytosis in one or more organs.

In another particular embodiment the invention provides the compounds of the invention or a pharmaceutical composition comprising one or more compounds of the invention for the treatment of a mammal suffering from excessive ferroptosis and oxytosis in one or more organs.

In another particular embodiment the invention provides the compounds of the invention or a pharmaceutical composition comprising one or more compounds of the invention for the treatment of diseases caused by excitatory amino acids. A well-known example of an excitatory amino acid is glutamine and the condition is designated as glutamine excitotoxicity.

In another particular embodiment the invention provides the compounds of the invention or a pharmaceutical composition comprising one or more compounds of the invention for the treatment of diseases caused by increased levels of intracellular reactive oxygen species (ROS).

In another particular embodiment the invention provides the compounds of the invention or a pharmaceutical composition comprising one or more compounds of the invention for the treatment of stroke, myocardial infarction, diabetes, sepsis, neurodegenerative diseases including Alzheimer's Disease, Parkinson's Disease, Amyotrophic lateral sclerosis, Huntington's Disease, Dementia with Lewy bodies, Friedreich's ataxia and multiple sclerosis. In a particular embodiment the invention provides the compounds of the invention or a pharmaceutical composition comprising one or more compounds of the invention for use in the prevention of transplant rejection. Thus the compounds can be used during the kidney, liver or heart transplantation to prevent organ damage due to ischemia-reperfusion injury.

In the present invention the potency of a compound inhibiting (or reducing) ferroptosis and/or oxytosis are determined in in vitro or in vivo assays. Typically in vitro assays are used to measure the potency of a candidate compound. Examples of suitable in vitro assays are cellular assays. One non-limiting example of an assay involves the use of the IMR-32 neuroblastoma cell line. The latter is stimulated to enter into ferroptosis upon stimulation with 10 μM erastin, a documented ferroptosis inducer (see for example Dixon et al (2012) *Cell* 149, 1060-1072 and ferroptosis inhibitors are evaluated for the prevention of erastin induced ferroptosis. Yet another assay is based the glutamate-induced cell death in the hippocampal cell line HT22 and ferroptosis/oxytosis inhibitors are evaluated for the prevention of cell death (see Henke N. et al (2013) *Cell Death and Disease* 4, e470). Still another assay is based on the sorafinib induced cell death (described to be iron dependent cell death) in hepatocellular carcinoma cells and ferroptosis inhibitors are evaluated for the prevention of cell death (see Louandre C. et al (2013) *Int. J. Cancer* 133, 1732). The calculated potency of a compound inhibiting ferroptosis and/or oxytosis is typically depicted as an IC50 value. Examples of suitable in vivo assays are typically pre-clinical disease models of for example mice for the diseases benefiting the application of ferroptosis and/or oxytosis inhibitors, as described herein.

One non-limiting example of an in vivo assay is based on inducing liver damage in mice by administering the herbicide diquat dibromide monohydrate and ferroptosis inhibitors are evaluated based on reduced levels of liver transaminases in serum (see Ran Q et al (2004) *J. Biol. Chem.* 279, 53, 55137).

Combination Therapies:

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known therapeutic agents for the treatment of diseases mentioned herein, as well as with admixtures and combinations thereof. Particularly preferred combinations are necroptosis inhibitors (e.g. necrostatin-1) and ferroptosis inhibitors. Examples of these combinations are described in Linkerman et al 2014.

The term "treating" or "treatment" as stated throughout this document is used conventionally, e.g. the management or care of a subject for the purpose of combating, alleviating, reducing, relieving, improving the condition of a disease cited herein.

Dose and Administration:

Based upon standard laboratory techniques known to evaluate compounds useful for the treatment of diseases cited herein, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of the indications cited herein. The amount of the active ingredient to be administered in the treatment can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 50 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight. The average daily oral dosage regimen will preferably be from 0.01 to 100 mg/kg of total body weight. The average daily intrathecal dosage regimen will preferably be from 0.01 to 100 mg/kg of total body weight.

It is evident for the skilled artisan that the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Experimental Procedures for Chemical Synthesis

Unless otherwise stated, laboratory reagent grade solvents were used. Reagents were obtained from various commercial sources and were used without any prior purification. Characterization of all compounds was done with $^1$H and $^{13}$C NMR and mass spectrometry of which the spectra were recorded with a 400 MHz Bruker Avance III Nanobay spectrometer with Ultrashield. All obtained spectra were analysed using MestReNova analytical chemistry software. Chemical shifts are displayed in ppm and coupling constants are shown in hertz (Hz). ES mass spectra were obtained from an Esquire 3000plus Ion Trap Mass Spectrometer from Bruker Daltonics. Purities were determined with a HPLC system based either on mass determination or on UV detection. A Waters SQD ESI mass spectrometer was used in combination with a Waters TUV detector. Waters Acquity UPLC BEH C18 1.7 µm, 2.1 mm×50 mm column was used. The eluent was composed of two different solvents nl. solvent A consisted of water with 0.1% formic acid while solvent B consisted of acetonitrile with 0.1% formic acid. Two methods were used interchangeably on the HPLC system. Method I involved the following parameters: 0.15 min 95% A, 5% B, then in 1.85 min from 95% A, 5% B to 95% B, 5% A, then 0.25 min (0.350 mL/min), 95% B, 5% A. The wavelength for UV detection was 254 nm. Method II involved the following: flow 0.4 mL/min, 0.25 min 95% A, 5% B, then in 4.75 min to 95% B, 5% A, then 0.25 min 95% B, 5% A, followed by 0.75 min 95% A, 5% B. The wavelength for UV detection was 214 nm. During the chemical synthesis, flash purification was performed when necessary on a Biotage ISOLERA One flash system equipped with an internal variable dual wavelength diode array detector (200-400 nm). For normal phase purifications SNAP cartridges (10-340 g, flow rate of 10-100 mL/min) were used, and reversed phase purifications were done while using of KP-C18 containing cartridges. Dry sample loading was done by self-packing sample cartridges using silica and Celite® 545, respectively, for normal and reversed phase purifications. Gradients used varied for each purification. During the pharmacokinetic characterization, mouse and rat plasma were obtained from Innovative Research. Liver microsomes were purchased from Corning B. V. Life Sciences. The turbidity in the kinetic solubility experiments was measured using the UV/VIS spectrophotometer Synergy MX, Biotek with Gen5.

The following section comprises the synthetic procedures and analytical data for all compounds reported in this manuscript. Several synthetic procedures that were used in the preparation of intermediates and final products are summarized here as "General Procedures". The purities of all final products were found to be >95%, unless stated otherwise.

EXAMPLES

1. Compound Design

Our earlier published results (see WO2016075330) involved a thorough exploration of the SAR which provided the following results: (1) The replacement of the labile ester moiety with a sulfonamide greatly improved stability as well as potency (2) The cyclohexyl moiety was deemed to be the most ideal substituent in regard to both potency and lipophilicity. More bulky alkyl groups tend to have a negative effect on the solubility of the compounds and smaller moieties impair the potency of the molecules. (3) The introduction of an aromatic group on the 3-amino position greatly improved potency, but also further decreased the solubility of the compounds.[16]

The major drawback of our previously published molecules was their poor solubility. The terminal position of the aliphatic chain that was coupled to the sulfonamide moiety was identified for further derivatisation in order to increase the solubility of these compounds. A variety of solubility improving groups were introduced at this terminal $E_1$ position (see Scheme 1). The cyclohexylamine group was kept as in Fer-1 and the $E_2$ position (see Scheme 1) was further derivatized with benzylic and pyridinylic substituents in a similar fashion to the previously reported sulfonamide analogues. (see also FIG. 3)

2. Chemical Synthesis of Representative Compounds of the Invention

The newly synthesized follow-up series consisted of 21 novel inhibitors of which the general synthetic strategy is displayed in Scheme 1.

Scheme 1: General overview of the synthetic route.

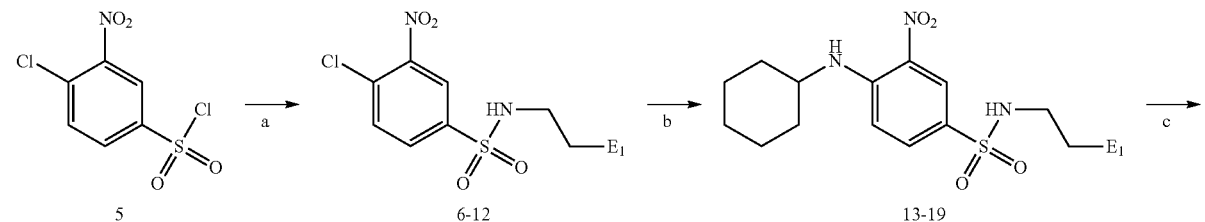

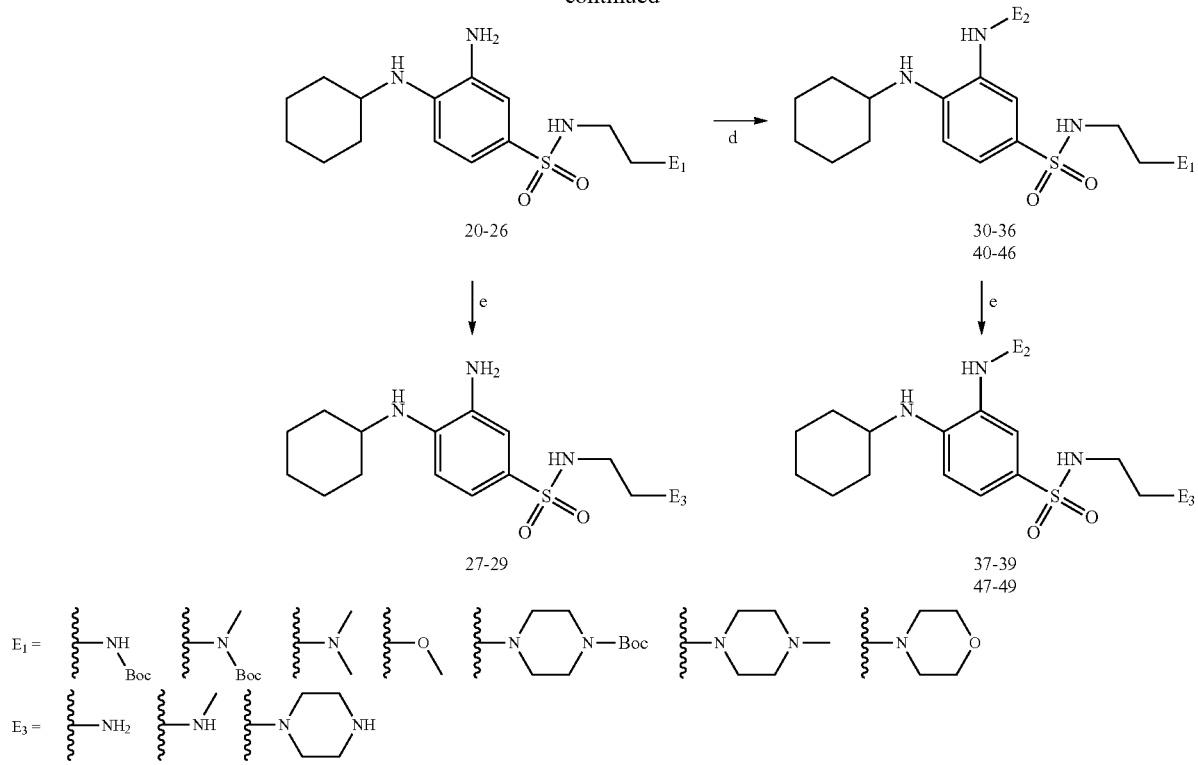

Reagents and conditions: (a) Aliphatic amine analogue, triethylamine, THF, 1 h, −40° C. (b) cyclohexylamine, $K_2CO_3$, DMSO, 18 h, 60° C. (c) Palladium hydroxide on carbon, $H_2$, methanol, 18 h, rt (d) benzylbromide or 4-(bromomethyl)pyridine hydrobromide, $K_2CO_3$, DMF. (e) HCl in dioxane, DCM All molecules were synthesized starting from 4-chloro-3-nitrobenzenesulfonyl chloride 5. Treatment of 5 with a solution containing the appropriate amine analogue resulted in the formation of 6-12. Subsequently a nucleophilic aromatic substitution of 6-12 with cyclohexylamine under basic conditions yielded 13-19. Palladium-catalyzed hydrogenation of the 3-nitro group to its corresponding amine resulted in the generation of molecules 20-26. Finally benzylic and pyridinylic substituents were introduced at the $E_2$-position to afford 30-36 and 40-46 respectively. If applicable, the protective Boc group was removed under acidic conditions to yield compounds 27-29, 37-39 and 47-49.

General Procedure A

A solution containing the appropriate aliphatic or cyclic amine substituent (1 equiv.) and triethylamine (2 equiv.) in THF was added dropwise to a solution containing 4-chloro-3-nitrobenzene-1-sulfonyl chloride 5 (1 equiv.) in THF that was cooled down to −40° C. After the addition was complete, the resulting mixture was allowed to warm up to room temperature over the course of one hour. Subsequently the reaction mixture was diluted with EtOAc and washed three times with water. The organic layer was dried using anhydrous sodium sulphate before being concentrated in vacuo. The crude reaction products 6-12 were used without any further purification.

General Procedure B

Intermediates 6-12 (1 equiv.) were dissolved in DMSO before potassium carbonate (2 equiv.) and cyclohexanamine (1.2 equiv.) were added. The resulting mixture was heated to a temperature of 60° C. and then stirred overnight. After cooling down to room temperature, the reaction mixture was diluted with EtOAc and washed three times with water. The organic layer was dried using anhydrous sodium sulphate before being concentrated in vacuo. If deemed necessary, further purification was conducted with flash chromatography on silica gel using a gradient consisting of heptanes and EtOAc to obtain intermediates 13-19.

General Procedure C

Intermediates 13-19 (1 equiv.) were dissolved in dry MeOH and the solution was purged using argon gas. Palladium(II) hydroxide was added under inert atmosphere while continuously stirring. After the addition was complete, the resulting mixture was put under hydrogen atmosphere and left to stir overnight. The reaction mixture was filtered through a patch of Celite® and then purified by flash chromatography on silica gel using a gradient consisting of heptanes and EtOAc to yield products 20-26.

General Procedure D

Compounds 20-26 (1 equiv.) were dissolved in DMF followed by the addition of potassium carbonate (1-3 equiv.) and the corresponding benzyl- or pyridinylderivate (1-2 equiv.). This mixture was allowed to stir at various temperatures and timespans, all of which are further specified at the corresponding compounds reported below. The crude product was then purified by either normal phase or reversed phase flash chromatography to yield compounds 30-36 and 40-46. The exact conditions of these purifications are reported below for each compound individually.

General Procedure E

Compounds 21-23, 31-33 and 41-43 (1 equiv.) were dissolved in dichloromethane followed by the addition of a 4M solution of hydrochloric acid in dioxane (8 equiv.) The reaction mixture was stirred at room temperature for 2 hours. After reaction diethylether was added to the reaction mixture in order to precipitate compounds 27-29, 37-39 and 47-49. The obtained HCl-salts were subsequently washed with a minimal amount of diethylether.

4-chloro-N-(2-(dimethylamino)ethyl)-3-nitrobenzenesulfonamide (6)

By following General Procedure A and using N,N-dimethylethane-1,2-diamine (1.38 g, 15.62 mmol) as the corresponding amine, the formation of 4-chloro-N-(2-(dimethylamino)ethyl)-3-nitrobenzenesulfonamide 6 (4.67 g, 15.16 mmol) was achieved. (Yield: 97%)
$^1$H NMR (400 MHz, DMSO-$d_6$) δ 2.07 (s, 6H), 2.25-2.30 (m, 2H), 2.97 (t, J=6.5 Hz, 2H), 8.05 (d, J=8.5 Hz, 1H), 8.12 (dd, J=8.5, 2.2 Hz, 1H), 8.50 (d, J=2.1 Hz, 1H).
$^{13}$C NMR (101 MHz, DMSO-d6) δ 40.62, 44.83, 58.06, 123.88, 128.93, 131.23, 132.84, 141.20, 147.31.

tert-butyl (2-((4-chloro-3-nitrophenyl)sulfonamido)ethyl)(methyl)carbamate (7)

By following General Procedure A and using tert-butyl (2-aminoethyl)(methyl)carbamate (2.04 g, 11.72 mmol) as the corresponding amine, the formation of tert-butyl (2-((4-chloro-3-nitrophenyl)sulfonamido)ethyl)(methyl)carbamate 7 (4.58 g, 11.62 mmol) was achieved. (Yield: 99%)
$^1$H NMR (400 MHz, Acetone-$d_6$) δ 1.42 (s, 9H), 2.83 (d, J=14.4 Hz, 3H), 3.20 (t, J=6.3 Hz, 2H), 3.31-3.42 (m, 2H), 7.03 (s, 1H), 8.00 (d, J=8.4 Hz, 1H), 8.15 (dd, J=8.5, 2.2 Hz, 1H), 8.45 (d, J=2.2 Hz, 1H).
$^{13}$C NMR (101 MHz, Acetone-$d_6$) δ 27.64, 41.25, 47.95, 48.67, 78.86, 124.14, 124.22, 129.91, 131.38, 133.07, 141.36, 148.03.

tert-butyl (2-((4-chloro-3-nitrophenyl)sulfonamido)ethyl)carbamate (8)

By following General Procedure A and using tert-butyl (2-aminoethyl)carbamate (3.28 g, 20.5 mmol) as the corresponding amine, the formation of tert-butyl (2-((4-chloro-3-nitrophenyl)sulfonamido)ethyl)carbamate 8 (6.2 g, 16.32 mmol) was achieved (Yield: 84%)
$^1$H NMR (400 MHz, Acetone-d6) δ 1.37 (s, 9H), 3.09-3.17 (m, 2H), 3.17-3.23 (m, 2H), 6.11 (t, J=6.0 Hz, 1H), 7.02 (t, J=5.7 Hz, 1H), 7.97 (d, J=8.5 Hz, 1H), 8.14 (dd, J=8.4, 2.2 Hz, 1H), 8.44 (d, J=2.2 Hz, 1H).
$^{13}$C NMR (101 MHz, Acetone-$d_6$) δ 27.74, 40.11, 43.17, 78.29, 124.27, 130.01, 131.43, 133.08, 141.28, 147.95, 156.09.

tert-butyl 4-(2-((4-chloro-3-nitrophenyl)sulfonamido)ethyl)piperazine-1-carboxylate (9)

By following General Procedure A and using 4-N-(2-Aminoethyl)-1-N-Boc-piperazine (3.76 g, 16.4 mmol) as the corresponding amine, the formation of tert-butyl 4-(2-((4-chloro-3-nitrophenyl)sulfonamido)ethyl)piperazine-1-carboxylate 9 (6.7 g, 16.32 mmol) was achieved (Yield: 96%)
$^1$H NMR (400 MHz, DMSO-$d_6$) δ 1.38 (s, 9H), 2.22 (t, J=5.0 Hz, 4H), 2.32 (t, J=6.5 Hz, 2H), 2.98 (q, J=5.3 Hz, 2H), 3.20 (dd, J=6.3, 3.6 Hz, 4H), 7.98-8.05 (m, 2H), 8.08 (dd, J=8.5, 2.1 Hz, 1H), 8.46 (d, J=2.1 Hz, 1H).
$^{13}$C NMR (101 MHz, DMSO-d6) δ 28.00, 43.05, 52.23, 56.69, 78.70, 123.82, 129.01, 131.24, 132.96, 141.12, 147.40, 153.72.

4-chloro-N-(2-(4-methylpiperazin-1-yl)ethyl)-3-nitrobenzenesulfonamide (10)

By following General Procedure A and using 2-(4-methylpiperazin-1-yl)ethanamine (2.24 g, 15.16 mmol) as the corresponding amine, the formation of 4-chloro-N-(2-(4-methylpiperazin-1-yl)ethyl)-3-nitrobenzenesulfonamide 10 (5.13 g, 14.14 mmol) was achieved. (Yield: 91%)
$^1$H NMR (400 MHz, DMSO-$d_6$) δ 2.09 (s, 3H), 2.12-2.26 (m, 8H), 2.29 (t, J=6.5 Hz, 2H), 2.97 (t, J=6.5 Hz, 2H), 8.02 (d, J=8.5 Hz, 1H), 8.08 (dd, J=8.5, 2.1 Hz, 1H), 8.45 (d, J=2.1 Hz, 1H).
$^{13}$C NMR (101 MHz, DMSO-$d_6$) δ 40.03, 45.63, 52.40, 54.39, 56.86, 123.81, 128.96, 131.21, 132.91, 141.33, 147.38.

4-chloro-N-(2-morpholinoethyl)-3-nitrobenzenesulfonamide (11)

By following General Procedure A and using 2-morpholinoethanamine (2.054 mL, 15.62 mmol) as the corresponding amine, the formation of 4-chloro-N-(2-morpholinoethyl)-3-nitrobenzenesulfonamide 11 (5.17 g, 14.78 mmol) was achieved. (Yield: 95%)
$^1$H NMR (400 MHz, DMSO-$d_6$) δ 2.22-2.27 (m, 4H), 2.30 (t, J=6.5 Hz, 2H), 2.93-3.02 (m, 2H), 3.43-3.48 (m, 4H), 8.02 (s, 1H), 8.03 (d, J=8.3 Hz, 1H), 8.08 (dd, J=8.5, 2.1 Hz, 1H), 8.46 (d, J=2.1 Hz, 1H).
$^{13}$C NMR (101 MHz, DMSO-$d_6$) δ 40.09, 52.99, 57.18, 65.92, 123.83, 128.99, 131.23, 132.94, 141.17, 147.39.

4-chloro-N-(2-methoxyethyl)-3-nitrobenzenesulfonamide (12)

By following General Procedure A and using 2-methoxyethanamine (1.42 g, 16.4 mmol) as the corresponding amine, the formation of 4-chloro-N-(2-methoxyethyl)-3-nitrobenzenesulfonamide 12 (4.2 g, 14.25 mmol) was achieved (Yield: 91%)
$^1$H NMR (400 MHz, Acetone-$d_6$) δ 3.18 (s, 3H), 3.22 (t, J=5.3 Hz, 2H), 3.38-3.45 (m, 2H), 6.86 (s, 1H), 7.93 (d, J=8.5 Hz, 1H), 8.14 (dd, J=8.5, 2.2 Hz, 1H), 8.44 (d, J=2.2 Hz, 1H).
$^{13}$C NMR (101 MHz, Acetone-$d_6$) δ 42.95, 57.83, 70.75, 124.28, 129.97, 131.50, 132.95, 141.48, 147.79.

4-(cyclohexylamino)-N-(2-(dimethylamino)ethyl)-3-nitrobenzenesulfonamide (13)

By following General Procedure B and using 4-chloro-N-(2-(dimethylamino)ethyl)-3-nitrobenzenesulfonamide 6 (4.665 g, 15.16 mmol) as the staring material, the formation of 4-(cyclohexylamino)-N-(2-(dimethylamino)ethyl)-3-nitrobenzenesulfonamide 13 (4.72 g, 12.74 mmol) was achieved. (Yield: 84%)
$^1$H NMR (400 MHz, DMSO-d6) δ 1.26-1.32 (m, 1H), 1.41-1.51 (m, 4H), 1.61-1.68 (m, 1H), 1.71-1.80 (m, 2H), 1.96-2.03 (m, 2H), 2.09 (s, 6H), 2.29 (t, J=6.8 Hz, 2H), 2.85 (t, J=6.8 Hz, 2H), 3.70-3.81 (m, 1H), 7.36 (d, J=9.3 Hz, 1H), 7.85 (dd, J=9.2, 2.3, 0.7 Hz, 1H), 8.32 (d, J=7.8 Hz, 1H), 8.49 (d, J=2.3 Hz, 1H).
$^{13}$C NMR (101 MHz, DMSO-$d_6$) δ 23.97, 24.92, 31.72, 40.58, 45.00, 50.63, 58.02, 115.89, 126.04, 126.17, 129.47, 133.34, 145.80.

tert-butyl (2-((4-(cyclohexylamino)-3-nitrophenyl)sulfonamido)ethyl)(methyl)carbamate (14)

By following General Procedure B and using tert-butyl (2-((4-chloro-3-nitrophenyl)sulfonamido)ethyl)(methyl)carbamate 7 (4.58 g, 11.62 mmol) as the starting material, the formation of tert-butyl (2-((4-(cyclohexylamino)-3-nitrophenyl)sulfonamido)ethyl)(methyl)carbamate 14 (3.46 g, 7.58 mmol) was achieved. (Yield: 65%)

$^1$H NMR (400 MHz, DMSO-d$_6$) δ 1.22-1.30 (m, 1H), 1.36 (s, 9H), 1.39-1.48 (m, 4H), 1.56-1.65 (m, 1H), 1.71 (dd, J=9.1, 4.7 Hz, 2H), 1.92-2.01 (m, 2H), 2.75 (s, 3H), 2.85 (t, J=6.7 Hz, 2H), 3.18 (t, J=6.7 Hz, 2H), 3.68-3.79 (m, 1H), 7.32 (d, J=9.2 Hz, 1H), 7.69 (s, 1H), 7.78 (dd, J=9.3, 2.3 Hz, 1H), 8.28 (d, J=7.8 Hz, 1H), 8.44 (d, J=2.3 Hz, 1H).

$^{13}$C NMR (101 MHz, DMSO-d$_6$) δ 24.44, 25.41, 28.45, 32.22, 41.02, 48.73, 51.16, 79.04, 116.52, 126.49, 126.54, 130.08, 133.74, 146.37, 155.07.

tert-butyl (2-((4-(cyclohexylamino)-3-nitrophenyl)sulfonamido)ethyl)carbamate (15)

By following General Procedure B and using tert-butyl (2-((4-chloro-3-nitrophenyl)sulfonamido)ethyl)carbamate 8 (3 g, 7.90 mmol) as the starting material, the formation of tert-butyl (2-((4-(cyclohexylamino)-3-nitrophenyl)sulfonamido)ethyl)carbamate 15 (3.3 g, 7.46 mmol) was achieved. (Yield: 94%)

$^1$H NMR (400 MHz, Acetone-d$_6$) δ 1.24-1.33 (m, 1H), 1.37 (s, 9H), 1.43-1.58 (m, 4H), 1.62-1.72 (m, 1H), 1.72-1.84 (m, 2H), 2.07-2.13 (m, 2H), 2.79 (s, 1H), 3.01 (q, J=6.3 Hz, 2H), 3.17 (q, J=6.0 Hz, 2H), 6.03 (s, 1H), 6.58 (t, J=6.1 Hz, 1H), 7.29 (dd, J=9.4, 2.9 Hz, 1H), 7.84 (dd, J=9.2, 2.4 Hz, 1H), 8.37 (d, J=7.7 Hz, 1H), 8.56 (d, J=2.4 Hz, 1H).

$^{13}$C NMR (101 MHz, Acetone-d$_6$) δ 24.24, 25.23, 27.66, 32.19, 40.07, 43.11, 51.19, 78.04, 115.56, 126.51, 126.69, 130.33, 133.45, 146.34, 155.96.

tert-butyl 4-(2-((4-(cyclohexylamino)-3-nitrophenyl)sulfonamido)ethyl)piperazine-1-carboxylate (16)

By following General Procedure B and using tert-butyl 4-(2-((4-chloro-3-nitrophenyl)sulfonamido)ethyl)piperazine-1-carboxylate 9 (6.7 g, 14.92 mmol) as the starting material, the formation of tert-butyl 4-(2-((4-(cyclohexylamino)-3-nitrophenyl)sulfonamido)ethyl)piperazine-1-carboxylate 16 (6.5 g, 12.7 mmol) was achieved. (Yield: 85%)

$^1$H NMR (400 MHz, DMSO-d6) δ 1.38 (s, 9H), 1.40-1.47 (m, 5H), 1.56-1.65 (m, 1H), 1.68-1.77 (m, 2H), 1.92-1.99 (m, 2H), 2.22 (t, J=5.0 Hz, 4H), 2.32 (t, J=6.7 Hz, 2H), 2.86 (t, J=6.7 Hz, 2H), 3.22 (t, J=5.0 Hz, 4H), 3.73 (d, J=9.3 Hz, 1H), 7.22 (s, 1H), 7.33 (d, J=9.3 Hz, 1H), 7.81 (ddd, J=9.3, 2.3, 0.7 Hz, 1H), 8.29 (d, J=7.8 Hz, 1H), 8.44 (d, J=2.2 Hz, 1H).

$^{13}$C NMR (101 MHz, DMSO-d$_6$) δ 23.97, 24.91, 28.00, 31.71, 42.79, 50.63, 52.29, 56.58, 78.66, 115.95, 126.04, 126.17, 129.48, 133.36, 145.81, 153.70.

4-(cyclohexylamino)-N-(2-(4-methylpiperazin-1-yl)ethyl)-3-nitrobenzenesulfonamide (17)

By following General Procedure B and using 4-chloro-N-(2-(4-methylpiperazin-1-yl)ethyl)-3-nitrobenzenesulfonamide 10 (5.1 g, 14.06 mmol) as the starting material, the formation of 4-(cyclohexylamino)-N-(2-(4-methylpiperazin-1-yl)ethyl)-3-nitrobenzenesulfonamide 17 (5.04 g, 11.84 mmol) was achieved. (Yield: 84%)

$^1$H NMR (400 MHz, DMSO-d$_6$) δ 1.21-1.31 (m, 1H), 1.37-1.47 (m, 4H), 1.57-1.65 (m, 1H), 1.67-1.76 (m, 2H), 1.91-1.99 (m, 2H), 2.09 (s, 3H), 2.12-2.26 (m, 8H), 2.29 (t, J=6.8 Hz, 2H), 2.84 (t, J=6.7 Hz, 2H), 3.68-3.78 (m, 1H), 7.31 (d, J=9.4 Hz, 1H), 7.80 (dd, J=9.2, 2.3, 0.6 Hz, 1H), 8.29 (d, J=7.8 Hz, 1H), 8.43 (d, J=2.3 Hz, 1H).

$^{13}$C NMR (101 MHz, DMSO-d$_6$) δ 23.96, 24.91, 31.73, 40.03, 45.69, 50.62, 52.51, 54.50, 56.77, 115.90, 126.03, 126.27, 129.50, 133.33, 145.81.

4-(cyclohexylamino)-N-(2-morpholinoethyl)-3-nitrobenzenesulfonamide (18)

By following General Procedure B and using 4-chloro-N-(2-morpholinoethyl)-3-nitrobenzenesulfonamide 11 (5.13 g, 14.66 mmol) as the starting material, the formation of 4-(cyclohexylamino)-N-(2-morpholinoethyl)-3-nitrobenzenesulfonamide 18 (5.3 g, 12.85 mmol) was achieved. (Yield: 88%)

$^1$H NMR (400 MHz, DMSO-d$_6$) δ 1.21-1.32 (m, 1H), 1.36-1.48 (m, 4H), 1.57-1.65 (m, 1H), 1.66-1.76 (m, 2H), 1.90-1.99 (m, 2H), 2.23-2.28 (m, 4H), 2.30 (t, J=6.7 Hz, 2H), 2.85 (t, J=6.7 Hz, 2H), 3.49 (t, J=4.6 Hz, 4H), 3.69-3.77 (m, 1H), 7.32 (d, J=9.3 Hz, 1H), 7.81 (dd, J=9.1, 2.2, 0.6 Hz, 1H), 8.29 (d, J=7.8 Hz, 1H), 8.44 (d, J=2.3 Hz, 1H).

$^{13}$C NMR (101 MHz, DMSO-d$_6$) δ 23.97, 24.92, 31.71, 40.11, 50.63, 53.08, 57.11, 66.00, 115.94, 126.05, 126.15, 129.48, 133.33, 145.81.

4-(cyclohexylamino)-N-(2-methoxyethyl)-3-nitrobenzenesulfonamide (19)

By following General Procedure B and using 4-chloro-N-(2-methoxyethyl)-3-nitrobenzenesulfonamide 12 (3 g, 10.18 mmol) as the starting material, the formation of 4-(cyclohexylamino)-N-(2-methoxyethyl)-3-nitrobenzenesulfonamide 19 (2.27 g, 6.36 mmol) was achieved. (Yield: 62.5%)

$^1$H NMR (400 MHz, DMSO-d6) δ 1.18-1.33 (m, 1H), 1.36-1.51 (m, 4H), 1.54-1.66 (m, 1H), 1.67-1.78 (m, 2H), 1.88-2.04 (m, 2H), 2.90 (q, J=5.6 Hz, 2H), 3.17 (s, 3H), 3.29-3.31 (m, 2H), 3.66-3.80 (m, 1H), 7.31 (d, J=9.3 Hz, 1H), 7.69 (t, J=5.8 Hz, 1H), 7.80 (dd, J=9.2, 2.3 Hz, 1H), 8.27 (d, J=7.8 Hz, 1H), 8.44 (d, J=2.2 Hz, 1H).

$^{13}$C NMR (101 MHz, DMSO-d$_6$) δ 24.45, 25.42, 32.23, 42.61, 51.14, 58.33, 70.98, 116.39, 126.53, 126.79, 130.03, 133.82, 146.33.

3-amino-4-(cyclohexylamino)-N-(2-(dimethylamino)ethyl)benzenesulfonamide (20)

By following General Procedure C and using 4-(cyclohexylamino)-N-(2-(dimethylamino)ethyl)-3-nitrobenzenesulfonamide 13 (4.72 g, 12.74 mmol) as the starting material, 3-amino-4-(cyclohexylamino)-N-(2-(dimethylamino)ethyl)benzenesulfonamide 20 (2.2 g, 6.46 mmol) was generated. (Yield: 51%)

$^1$H NMR (400 MHz, DMSO-d$_6$) δ 1.13-1.25 (m, 3H), 1.29-1.43 (m, 2H), 1.63 (dt, J=12.6, 3.6 Hz, 1H), 1.74 (dt, J=13.2, 3.7 Hz, 2H), 1.92-1.99 (m, 2H), 2.06 (s, 6H), 2.23 (t, 2H), 2.70-2.75 (m, 2H), 3.24-3.33 (m, 1H), 4.85 (d, J=7.5 Hz, 1H), 4.95 (s, 2H), 6.50 (d, J=9.0 Hz, 1H), 6.81-6.86 (m, 1H), 6.90-6.95 (m, 2H).

$^{13}$C NMR (101 MHz, DMSO-d$_6$) δ 24.66, 25.55, 32.53, 40.63, 45.08, 50.69, 58.00, 107.91, 111.49, 117.19, 125.77, 134.44, 138.06.

t$_R$ 1.32 min, MS (ESI) m/z 341 [M+H] (100%)

tert-butyl (2-((3-amino-4-(cyclohexylamino)phenyl)sulfonamido)ethyl)(methyl)carbamate (21)

By following General Procedure C and using tert-butyl (2-((4-(cyclohexylamino)-3-nitrophenyl)sulfonamido)ethyl)

(methyl)carbamate 14 (3.46 g, 7.58 mmol) as starting material, tert-butyl (2-((3-amino-4-(cyclohexylamino)phenyl)sulfonamido)ethyl)(methyl)carbamate 21 (1.98 g, 4.64 mmol) was generated. (Yield: 61.2%)

$^1$H NMR (400 MHz, DMSO-d$_6$) δ 1.13-1.27 (m, 3H), 1.33-1.40 (m, 11H), 1.63 (dt, J=12.7, 3.7 Hz, 1H), 1.74 (dt, J=13.3, 3.6 Hz, 2H), 1.92-2.00 (m, 2H), 2.71-2.80 (m, 5H), 3.15 (t, J=6.9 Hz, 2H), 3.23-3.33 (m, 1H), 4.86 (d, J=7.5 Hz, 1H), 4.96 (s, 2H), 6.50 (d, J=8.9 Hz, 1H), 6.90-6.95 (m, 2H), 7.11 (s, 1H).

$^{13}$C NMR (101 MHz, DMSO-d$_6$) δ 24.66, 25.55, 27.99, 32.52, 34.83, 40.66, 48.24, 50.68, 78.51, 107.86, 111.38, 117.14, 125.72, 134.48, 138.09, 154.57.

tert-butyl (2-((3-amino-4-(cyclohexylamino)phenyl)sulfonamido)ethyl)carbamate (22)

By following General Procedure C and using tert-butyl (2-((4-(cyclohexylamino)-3-nitrophenyl)sulfonamido)ethyl)carbamate 15 (2.7 g, 6.1 mmol) as starting material, tert-butyl (2-((3-amino-4-(cyclohexylamino)phenyl)sulfonamido)ethyl)carbamate 22 (1.5 g, 3.64 mmol) was generated. (Yield: 59.6%)

$^1$H NMR (400 MHz, DMSO-d$_6$) δ 1.15-1.27 (m, 3H), 1.36 (s, 11H), 1.55-1.68 (m, 1H), 1.70-1.78 (m, 2H), 1.92-2.03 (m, 2H), 2.67 (q, J=6.6, 6.1 Hz, 2H), 2.95 (q, J=6.7 Hz, 2H), 3.24-3.30 (m, 1H), 4.83 (d, J=7.5 Hz, 1H), 4.93 (s, 2H), 6.50 (d, J=8.8 Hz, 1H), 6.71 (d, J=6.4 Hz, 1H), 6.88-6.94 (m, 2H), 6.97-7.05 (m, 1H).

$^{13}$C NMR (101 MHz, DMSO-d$_6$) δ 25.15, 26.04, 28.66, 31.78, 33.05, 42.87, 51.22, 78.20, 108.42, 111.97, 117.68, 126.27, 134.95, 138.65, 155.95.

tert-butyl 4-(2-((3-amino-4-(cyclohexylamino)phenyl)sulfonamido)ethyl)piperazine-1-carboxylate (23)

By following General Procedure C and using tert-butyl 4-(2-((4-(cyclohexylamino)-3-nitrophenyl)sulfonamido)ethyl)piperazine-1-carboxylate 16 (6.5 g, 12.7 mmol) as starting material, tert-butyl 4-(2-((3-amino-4-(cyclohexylamino)phenyl)sulfonamido)ethyl)piperazine-1-carboxylate 23 (3.9 g, 8.1 mmol) was generated. (Yield: 63.7%)

$^1$H NMR (400 MHz, DMSO-d$_6$) δ 1.12-1.27 (m, 3H), 1.29-1.36 (m, 2H), 1.39 (s, 9H), 1.58-1.68 (m, 1H), 1.68-1.78 (m, 2H), 1.90-2.01 (m, 2H), 2.21 (t, J=5.3 Hz, 4H), 2.30 (dd, J=7.7, 6.2 Hz, 2H), 2.77 (dt, J=7.7, 6.0 Hz, 2H), 3.24 (t, J=5.1 Hz, 4H), 3.27-3.32 (m, 1H), 4.85 (d, J=7.5 Hz, 1H), 4.95 (s, 2H), 6.50 (d, J=9.0 Hz, 1H), 6.81 (t, J=5.8 Hz, 1H), 6.93 (dq, J=4.3, 2.2 Hz, 2H).

$^{13}$C NMR (101 MHz, DMSO-d6) δ 24.65, 25.55, 28.01, 30.65, 32.52, 42.98, 50.70, 52.33, 56.54, 78.65, 107.92, 111.50, 117.24, 125.69, 134.47, 138.09, 153.71.

3-amino-4-(cyclohexylamino)-N-(2-(4-methylpiperazin-1-yl)ethyl)benzenesulfonamide (24)

By following General Procedure C and using 4-(cyclohexylamino)-N-(2-(4-methylpiperazin-1-yl)ethyl)-3-nitrobenzenesulfonamide 17 (5.0 g, 11.75 mmol) as starting material, 3-amino-4-(cyclohexylamino)-N-(2-(4-methylpiperazin-1-yl)ethyl)benzenesulfonamide 24 (3.00 g, 7.58 mmol) was generated. (Yield: 64.5%)

$^1$H NMR (400 MHz, DMSO-d$_6$) δ 1.11-1.26 (m, 3H), 1.29-1.43 (m, 2H), 1.58-1.67 (m, 1H), 1.69-1.78 (m, 2H), 1.93-1.99 (m, 2H), 2.11 (s, 3H), 2.14-2.35 (m, 10H), 2.68-2.77 (m, 2H), 3.23-3.34 (m, 1H), 4.86 (d, J=7.5 Hz, 1H), 4.96 (s, 2H), 6.49 (d, J=9.0 Hz, 1H), 6.81 (t, J=5.8 Hz, 1H), 6.90-6.94 (m, 2H).

$^{13}$C NMR (101 MHz, DMSO-d$_6$) δ 24.66, 25.55, 32.52, 40.10, 45.71, 50.68, 52.53, 54.59, 56.67, 107.90, 111.46, 117.19, 125.63, 134.45, 138.06.

t$_R$ 1.29 min, MS (ESI) m/z 396 [M+H] (100%)

3-amino-4-(cyclohexylamino)-N-(2-morpholinoethyl)benzenesulfonamide (25)

By following General Procedure C and using 4-(cyclohexylamino)-N-(2-morpholinoethyl)-3-nitrobenzenesulfonamide 18 (5.3 g, 12.85 mmol) as starting material, 3-amino-4-(cyclohexylamino)-N-(2-morpholinoethyl)benzenesulfonamide 25 (3.4 g, 8.89 mmol) was generated. (Yield: 69.2%)

$^1$H NMR (400 MHz, DMSO-d$_6$) δ 1.13-1.28 (m, 3H), 1.29-1.43 (m, 2H), 1.63 (dt, J=12.5, 3.8 Hz, 1H), 1.70-1.79 (m, 2H), 1.92-1.99 (m, 2H), 2.23-2.32 (m, 6H), 2.77 (dt, J=7.6, 5.9 Hz, 2H), 3.23-3.34 (m, 1H), 3.49-3.52 (m, 4H), 4.84 (d, J=7.5 Hz, 1H), 4.95 (s, 2H), 6.50 (d, J=9.0 Hz, 1H), 6.82 (t, J=11.7, 5.9 Hz, 1H), 6.92-6.95 (m, 2H).

$^{13}$C NMR (101 MHz, DMSO-d6) δ 24.65, 25.55, 32.52, 39.79, 50.69, 53.12, 57.06, 66.06, 107.90, 111.51, 117.24, 125.68, 134.46, 138.10.

t$_R$ 1.31 min, MS (ESI) m/z 383 [M+H] (100%)

3-amino-4-(cyclohexylamino)-N-(2-methoxyethyl)benzenesulfonamide (26)

By following General Procedure C and using 4-(cyclohexylamino)-N-(2-methoxyethyl)-3-nitrobenzenesulfonamide 19 (3.5 g, 9.79 mmol) as starting material, 3-amino-4-(cyclohexylamino)-N-(2-methoxyethyl)benzenesulfonamide 26 (2.13 g, 6.51 mmol) was generated. (Yield: 66.5%)

$^1$H NMR (400 MHz, DMSO-d$_6$) δ 1.15-1.25 (m, 3H), 1.28-1.43 (m, 2H), 1.58-1.67 (m, 1H), 1.69-1.79 (m, 2H), 1.91-2.02 (m, 2H), 2.81 (q, J=6.1 Hz, 2H), 3.19 (s, 3H), 3.26-3.33 (m, 3H), 4.82 (d, J=7.5 Hz, 1H), 4.92 (s, 2H), 6.50 (d, J=8.9 Hz, 1H), 6.92 (s, 1H), 6.94 (d, J=2.2 Hz, 1H), 7.03 (t, J=6.1 Hz, 1H).

$^{13}$C NMR (101 MHz, DMSO-d$_6$) δ 25.14, 26.05, 33.04, 42.53, 51.21, 58.36, 71.08, 108.44, 112.05, 117.71, 126.45, 134.94, 138.64.

t$_R$ 1.58 min, MS (ESI) m/z 328 [M+H] (100%)

3-amino-4-(cyclohexylamino)-N-(2-(methylamino)ethyl)benzenesulfonamide Hydrochloride (27)

By following General Procedure E using tert-butyl (2-((3-amino-4-(cyclohexylamino)phenyl)sulfonamido)ethyl)(methyl)carbamate 21 (0.1 g, 0.23 mmol) as starting material to afford the desired 3-amino-4-(cyclohexylamino)-N-(2-(methylamino)ethyl)benzenesulfonamide hydrochloride 27 (0.024 g, 0.067 mmol). (Yield: 28.6%) The reported NMR spectrum is that of the hydrochloric acid form of 27.

$^1$H NMR (400 MHz, DMSO-d$_6$) δ 1.14-1.26 (m, 3H), 1.29-1.45 (m, 2H), 1.57-1.67 (m, 1H), 1.69-1.79 (m, 2H), 1.92-1.99 (m, 2H), 2.18 (s, 3H), 2.46 (t, J=6.6 Hz, 2H), 2.72 (t, J=6.6 Hz, 2H), 3.23-3.37 (m, 1H), 4.85 (d, J=7.5 Hz, 1H), 4.95 (s, 2H), 6.47-6.53 (m, 1H), 6.90-6.95 (m, 2H).

$^{13}$C NMR (101 MHz, DMSO-d$_6$) δ 24.66, 25.55, 32.53, 35.53, 42.02, 50.40, 50.69, 107.89, 111.47, 117.17, 125.77, 134.42, 138.04.

t$_R$ 1.26 min, MS (ESI) m/z 327 [M+H] (100%)

3-amino-N-(2-aminoethyl)-4-(cyclohexylamino) benzenesulfonamide Hydrochloride (28)

By following General Procedure E using tert-butyl (2-((3-amino-4-(cyclohexylamino)phenyl)sulfonamido)ethyl) carbamate 22 (0.15 g, 0.36 mmol) as starting material to afford the desired 3-amino-N-(2-aminoethyl)-4-(cyclohexylamino)benzenesulfonamide hydrochloride 28 (0.046 g, 0.132 mmol). (Yield: 36.3%) The reported NMR spectrum is that of the free base of 28.

$^1$H NMR (400 MHz, DMSO-d$_6$) δ 1.10-1.44 (m, 7H), 1.58-1.69 (m, 1H), 1.69-1.79 (m, 2H), 1.93-2.00 (m, 2H), 2.51-2.55 (m, 2H), 2.66 (t, J=6.3 Hz, 2H), 4.85 (d, J=7.4 Hz, 1H), 4.95 (s, 2H), 6.50 (d, J=9.0 Hz, 1H), 6.88-6.97 (m, 2H).

$^{13}$C NMR (101 MHz, DMSO-d$_6$) δ 24.67, 25.55, 32.54, 41.13, 45.87, 50.68, 107.87, 111.46, 117.16, 125.88, 134.40, 138.02.

t$_R$ 1.17 min, MS (ESI) m/z 313 [M+H] (100%)

3-amino-4-(cyclohexylamino)-N-(2-(piperazin-1-yl) ethyl)benzenesulfonamide (29)

By following General Procedure E using tert-butyl 4-(2-((3-amino-4-(cyclohexylamino)phenyl)sulfonamido)ethyl) piperazine-1-carboxylate 23 (0.15 g, 0.36 mmol) as starting material to afford the desired 3-amino-4-(cyclohexylamino)-N-(2-(piperazin-1-yl)ethyl)benzenesulfonamide 29 (0.120 g, 0.289 mmol). (Yield: 69.1%) The reported NMR spectrum is that of the free base of 29.

$^1$H NMR (400 MHz, DMSO-d$_6$) δ 1.14-1.26 (m, 4H), 1.29-1.43 (m, 2H), 1.58-1.68 (m, 1H), 1.68-1.78 (m, 2H), 1.91-2.03 (m, 2H), 2.13-2.21 (m, 4H), 2.22-2.29 (m, 2H), 2.62 (t, J=4.9 Hz, 4H), 2.74 (t, J=7.1 Hz, 2H), 3.26-3.30 (m, 1H), 4.86 (d, J=7.5 Hz, 1H), 4.96 (s, 2H), 6.50 (d, J=9.0 Hz, 1H), 6.74-6.84 (m, 1H), 6.87-6.96 (m, 2H).

$^{13}$C NMR (101 MHz, DMSO-d6) δ 24.66, 25.55, 32.52, 45.38, 50.68, 53.96, 57.41, 107.89, 111.47, 117.20, 125.60, 134.45, 138.07.

t$_R$ 1.17 min, MS (ESI) m/z 381 [M+H] (100%)

3-(benzylamino)-4-(cyclohexylamino)-N-(2-(dimethylamino)ethyl)benzenesulfonamide (30)

By following General Procedure D, the reaction mixture was prepared using 3-amino-4-(cyclohexylamino)-N-(2-(dimethylamino)ethyl)benzenesulfonamide 20 (0.300 g, 0.881 mmol, 1 equiv.), bromomethylbenzene (0.105 mL, 0.881 mmol, 1 equiv.) and potassium carbonate (0.122 g, 0.881 mmol, 1 equiv.). This mixture was allowed to stir for 15 minutes at room temperature. The mixture was diluted with water and washed with EtOAc. The aqueous layer was concentrated, lyophilisated and purified further using reverse phase flash chromatography (Water/MeOH) to afford the desired 3-(benzylamino)-4-(cyclohexylamino)-N-(2-(dimethylamino)ethyl)benzenesulfonamide 30 (0.151 g, 0.351 mmol) (Yield: 40%)

$^1$H NMR (400 MHz, Acetone-d6) δ 1.18-1.48 (m, 5H), 1.61-1.70 (m, 1H), 1.74-1.82 (m, 2H), 2.01-2.09 (m, 2H), 3.32 (s, 6H), 3.35-3.42 (m, 1H), 3.50 (t, J=5.9 Hz, 2H), 3.79 (t, J=6.0 Hz, 2H), 4.76-4.82 (m, 2H), 4.97 (s, 2H), 6.58 (d, J=8.4 Hz, 1H), 7.18 (dd, J=8.4, 2.2 Hz, 1H), 7.35 (d, J=2.2 Hz, 1H), 7.47-7.57 (m, 3H), 7.75-7.78 (m, 2H).

$^{13}$C NMR (101 MHz, Acetone-d$_6$) δ 25.85, 26.66, 33.72, 38.36, 50.91, 52.23, 64.79, 68.57, 109.18, 114.01, 119.81, 126.66, 128.97, 129.83, 131.29, 134.32, 135.67, 140.63.

t$_R$ 1.51 min, MS (ESI) m/z 431 [M+H] (100%)

tert-butyl(2-((3-(benzylamino)-4-(cyclohexylamino) phenyl)sulfonamido)ethyl)(methyl)carbamate (31)

By following General Procedure D, the reaction mixture was prepared using tert-butyl (2-((3-amino-4-(cyclohexylamino)phenyl)sulfonamido)ethyl)(methyl)carbamate 21 (0.100 g, 0.234 mmol, 1 equiv.), bromomethylbenzene (0.028 mL, 0.234 mmol, 1 equiv.) and potassium carbonate (0.032 g, 0.234 mmol, 1 equiv.). This mixture was allowed to stir for 45 minutes at 40° C. The mixture was diluted with water and washed with EtOAc. The organic layer was concentrated to afford tert-butyl (2-((3-(benzylamino)-4-(cyclohexylamino)phenyl)sulfonamido)ethyl)(methyl)carbamate 31 which was introduced in the next step without further purification.

tert-butyl (2-((3-(benzylamino)-4-(cyclohexylamino) phenyl)sulfonamido)ethyl)carbamate (32)

By following General Procedure D, the reaction mixture was prepared using tert-butyl (2-((3-amino-4-(cyclohexylamino)phenyl)sulfonamido)ethyl)carbamate 22 (0.200 g, 0.485 mmol, 1 equiv.), bromomethylbenzene (0.058 mL, 0.485 mmol, 1 equiv.) and potassium carbonate (0.080 g, 0.485 mmol, 1 equiv.). This mixture was allowed to stir for 60 minutes at 40° C. The mixture was diluted with water and washed with EtOAc. The organic layer was concentrated to afford tert-butyl (2-((3-(benzylamino)-4-(cyclohexylamino) phenyl)sulfonamido)ethyl)carbamate 32 which was introduced in the next step without further purification.

tert-butyl 4-(2-((3-(benzylamino)-4-(cyclohexylamino)phenyl)sulfonamido)ethyl)piperazine-1-carboxylate (33)

By following General Procedure D, the reaction mixture was prepared using tert-butyl 4-(2-((3-amino-4-(cyclohexylamino)phenyl)sulfonamido)ethyl)piperazine-1-carboxylate 23 (0.300 g, 0.623 mmol, 1 equiv.), bromomethylbenzene (0.074 mL, 0.623 mmol, 1 equiv.) and potassium carbonate (0.172 g, 0.623 mmol, 1 equiv.). This mixture was allowed to stir for 60 minutes at 40° C. The mixture was diluted with water and washed with EtOAc. The aqueous layer was concentrated and purified further using normal phase flash chromatography (Heptane/Ethyl acetate) to afford the desired tert-butyl 4-(2-((3-(benzylamino)-4-(cyclohexylamino)phenyl)sulfonamido)ethyl)piperazine-1-carboxylate 33 (0.135 g, 0.236 mmol) (Yield: 37.9%)

$^1$H NMR (400 MHz, DMSO-d6) δ 1.14-1.30 (m, 3H), 1.32-1.38 (m, 2H), 1.39 (s, 9H), 1.60-1.69 (m, 1H), 1.70-1.80 (m, 2H), 1.94-2.05 (m, 2H), 2.10-2.19 (m, 4H), 2.21 (t, J=6.8 Hz, 2H), 2.55-2.64 (m, 2H), 3.17-3.28 (m, 4H), 3.29-3.35 (m, 1H), 4.32 (d, J=5.4 Hz, 2H), 5.13 (d, J=7.2 Hz, 1H), 5.69 (t, J=5.6 Hz, 1H), 6.55 (d, J=8.5 Hz, 1H), 6.73 (d, J=2.1 Hz, 1H), 6.78 (t, J=5.8 Hz, 1H), 6.98 (dd, J=8.3, 2.1 Hz, 1H), 7.21-7.41 (m, 5H).

$^{13}$C NMR (101 MHz, DMSO-d$_6$) δ 24.67, 25.57, 28.01, 32.46, 42.67, 43.67, 46.89, 50.85, 52.20, 56.43, 78.66, 107.49, 117.22, 125.80, 126.77, 127.33, 128.28, 134.49, 138.33, 139.42, 153.70.

3-(benzylamino)-4-(cyclohexylamino)-N-(2-(4-methylpiperazin-1-yl)ethyl)benzenesulfonamide (34)

By following General Procedure D, the reaction mixture was prepared using 3-amino-4-(cyclohexylamino)-N-(2-(4- methylpiperazin-1-yl)ethyl)benzenesulfonamide 24 (0.200 g, 0.506 mmol, 1 equiv.), bromomethylbenzene (0.060 mL, 0.506 mmol, 1 equiv.) and potassium carbonate (0.070 g, 0.506 mmol, 1 equiv.). This mixture was allowed to stir for 10 minutes at room temperature. The mixture was diluted with water and washed with EtOAc. The aqueous layer was concentrated, lyophilisated and purified further using reverse phase flash chromatography (Water/MeOH) to afford the desired 3-(benzylamino)-4-(cyclohexylamino)-N-(2-(4-methylpiperazin-1-yl)ethyl)benzenesulfonamide 34 (0.066 g, 0.136 mmol) (Yield: 26.9%)

$^1$H NMR (400 MHz, Methanol-$d_4$) δ 1.21-1.35 (m, 3H), 1.36-1.52 (m, 2H), 1.66-1.75 (m, 1H), 1.81 (dt, J=13.3, 3.4 Hz, 2H), 2.00-2.12 (m, 2H), 2.53 (dd, J=6.6, 5.2 Hz, 2H), 2.62 (ddd, J=13.2, 9.7, 2.7 Hz, 2H), 2.78 (dt, J=13.5, 3.7 Hz, 2H), 2.94-3.06 (m, 5H), 3.26-3.30 (m, 2H), 3.35-3.41 (m, 1H), 3.43-3.56 (m, 2H), 4.62 (s, 2H), 6.63 (d, J=8.4 Hz, 1H), 7.18-7.25 (m, 2H), 7.50-7.64 (m, 5H).

$^{13}$C NMR (101 MHz, Methanol-$d_4$) δ 26.28, 27.05, 34.10, 41.03, 47.05, 52.70, 56.40, 61.04, 69.95, 109.77, 114.53, 120.83, 127.11, 128.24, 130.36, 131.95, 134.46, 135.33, 141.30.

$t_R$ 1.48 min, MS (ESI) m/z 486 [M+H] (100%)

3-(benzylamino)-4-(cyclohexylamino)-N-(2-morpholinoethyl)benzenesulfonamide (35)

By following General Procedure D, the reaction mixture was prepared using 3-amino-4-(cyclohexylamino)-N-(2-morpholinoethyl)benzenesulfonamide 25 (0.300 g, 0.784 mmol, 1 equiv.), bromomethylbenzene (0.094 mL, 0.784 mmol, 1 equiv.) and potassium carbonate (0.108 g, 0.784 mmol, 1 equiv.). This mixture was allowed to stir for 20 minutes at 40° C. The mixture was diluted with water and washed with EtOAc. The aqueous layer was concentrated, lyophilisated and purified further using reverse phase flash chromatography (Water/MeOH) to afford the desired 3-(benzylamino)-4-(cyclohexylamino)-N-(2-morpholinoethyl)benzenesulfonamide 35. (0.065 g, 0.138 mmol.) (Yield: 17.5%)

$^1$H NMR (400 MHz, Acetone-$d_6$) δ 1.21-1.33 (m, 3H), 1.38-1.51 (m, 2H), 1.64-1.70 (m, 1H), 1.74-1.83 (m, 2H), 2.05-2.13 (m, 2H), 2.16-2.20 (m, 4H), 2.28 (t, J=6.6, 5.8 Hz, 2H), 2.76 (q, J=6.4, 5.7 Hz, 2H), 3.39-3.49 (m, 1H), 3.52 (t, 4H), 4.40 (d, J=5.4 Hz, 2H), 4.65 (t, J=7.2 Hz, 1H), 4.84 (t, J=5.5 Hz, 1H), 5.57 (t, J=5.6 Hz, 1H), 6.71 (d, J=8.4 Hz, 1H), 7.01 (d, J=2.1 Hz, 1H), 7.18 (dd, J=8.3, 2.1 Hz, 1H), 7.24-7.30 (m, 1H), 7.32-7.38 (m, 2H), 7.40-7.44 (m, 2H).

$^{13}$C NMR (101 MHz, Acetone-$d_6$) δ 25.76, 26.68, 33.74, 40.37, 48.73, 52.26, 54.01, 57.47, 67.31, 109.35, 110.47, 119.54, 127.76, 127.89, 128.55, 129.31, 136.11, 140.37, 140.61.

$t_R$ 1.66 min, MS (ESI) m/z 473 [M+H] (100%)

3-(benzylamino)-4-(cyclohexylamino)-N-(2-methoxyethyl)benzenesulfonamide (36)

By following General Procedure D, the reaction mixture was prepared using 3-amino-4-(cyclohexylamino)-N-(2-methoxyethyl)benzenesulfonamide 26 (0.300 g, 0.916 mmol, 1 equiv.), bromomethylbenzene (0.110 mL, 0.916 mmol, 1 equiv.) and potassium carbonate (0.127 g, 0.916 mmol, 1 equiv.). This mixture was allowed to stir for 4 hours at 60° C. The mixture was diluted with EtOAc and washed with water. The organic layer was dried using anhydrous sodium sulfate, concentrated and purified further using preparative HPLC (Water/Acetonitrile) to afford the desired 3-(benzylamino)-4-(cyclohexylamino)-N-(2-methoxyethyl)benzenesulfonamide 36 (0.020 g, 0.048 mmol) (Yield: 5.23%)

$^1$H NMR (400 MHz, Methanol-$d_4$) δ 1.22-1.36 (m, 3H), 1.36-1.53 (m, 2H), 1.66-1.77 (m, 1H), 1.83 (dt, J=13.1, 3.7 Hz, 2H), 2.11 (dd, J=13.3, 3.4 Hz, 2H), 2.72 (t, J=5.6 Hz, 2H), 3.23 (d, J=3.5 Hz, 5H), 3.37-3.42 (m, 1H), 4.40 (s, 2H), 6.62-6.67 (m, 1H), 6.89 (d, J=2.1 Hz, 1H), 7.15 (dd, J=8.4, 2.1 Hz, 1H), 7.21-7.27 (m, 1H), 7.32 (ddd, J=7.6, 6.8, 1.2 Hz, 2H), 7.39 (ddt, J=7.7, 1.5, 0.7 Hz, 2H).

$^{13}$C NMR (101 MHz, Methanol-$d_4$) δ 26.29, 27.10, 34.11, 43.57, 48.89, 52.82, 58.84, 72.03, 109.62, 110.66, 119.71, 127.10, 128.04, 128.60, 129.54, 136.35, 140.80, 141.25.

$t_R$ 2.18 min, MS (ESI) m/z 418 [M+H] (100%)

3-(benzylamino)-4-(cyclohexylamino)-N-(2-(methylamino)ethyl)benzenesulfonamide Hydrochloride (37)

By following General Procedure E using tert-butyl (2-((3-(benzylamino)-4-(cyclohexylamino)phenyl)sulfonamido)ethyl)(methyl)carbamate 31 (0.300 g, 0.581 mmol) as starting material to afford the desired 3-(benzylamino)-4-(cyclohexylamino)-N-(2-(methylamino)ethyl)benzenesulfonamide hydrochloride 37 (0.075 g, 0.166 mmol). (Yield: 28.5%) The reported NMR spectrum is that of the free base of 37.

$^1$H NMR (400 MHz, DMSO-d6) δ 1.14-1.29 (m, 3H), 1.30-1.44 (m, 2H), 1.59-1.69 (m, 1H), 1.70-1.82 (m, 2H), 1.95-2.03 (m, 2H), 2.15 (s, 3H), 2.37 (t, J=6.4 Hz, 2H), 2.55 (t, J=6.4 Hz, 2H), 3.30-3.42 (m, 1H), 4.32 (d, J=5.3 Hz, 2H), 5.14 (d, J=7.2 Hz, 1H), 5.69 (t, J=5.6 Hz, 1H), 6.54 (d, J=8.4 Hz, 1H), 6.72 (d, J=2.1 Hz, 1H), 6.96 (dd, J=8.3, 2.1 Hz, 1H), 7.20-7.43 (m, 5H).

$^{13}$C NMR (101 MHz, DMSO-$d_6$) δ 24.68, 25.57, 32.47, 35.50, 41.90, 46.91, 50.30, 50.85, 107.43, 117.16, 125.92, 126.78, 127.37, 128.29, 134.50, 138.32, 139.40.

$t_R$ 1.82 min, MS (ESI) m/z 417 [M+H] (100%)

N-(2-aminoethyl)-3-(benzylamino)-4-(cyclohexylamino)benzenesulfonamide Hydrochloride (38)

By following General Procedure E using tert-butyl (2-((3-(benzylamino)-4-(cyclohexylamino)phenyl)sulfonamido)ethyl)carbamate 32 (0.150 g, 0.298 mmol) as starting material to afford the desired N-(2-aminoethyl)-3-(benzylamino)-4-(cyclohexylamino)benzenesulfonamide hydrochloride 38 (0.034 g, 0.078 mmol). (Yield: 26.1%) The reported NMR spectrum is that of the hydrochloric salt of 38.

$^1$H NMR (400 MHz, DMSO-$d_6$) δ 1.12-1.29 (m, 3H), 1.31-1.45 (m, 2H), 1.64 (m, 1H), 1.70-1.82 (m, 2H), 1.94-2.06 (m, 2H), 2.38-2.45 (m, 2H), 2.45-2.49 (m, 2H), 3.25-3.41 (m, 1H), 4.32 (d, J=5.3 Hz, 2H), 5.13 (d, J=7.2 Hz, 1H), 5.68 (t, J=5.6 Hz, 1H), 6.54 (d, J=8.4 Hz, 1H), 6.71 (d, J=2.1 Hz, 1H), 6.96 (dd, J=8.4, 2.1 Hz, 1H), 7.20-7.30 (m, 1H), 7.30-7.42 (m, 4H).

$^{13}$C NMR (101 MHz, DMSO-$d_6$) δ 24.69, 25.57, 32.49, 41.16, 46.07, 46.92, 50.86, 107.43, 117.14, 126.08, 126.78, 127.38, 128.30, 134.48, 138.29, 139.39.

$t_R$ 1.81 min, MS (ESI) 403 m/z [M+H] (100%)

3-(benzylamino)-4-(cyclohexylamino)-N-(2-(piperazin-1-yl)ethyl)benzenesulfonamide Hydrochloride (39)

By following General Procedure E using tert-butyl 4-(2-((3-(benzylamino)-4-(cyclohexylamino)phenyl)sulfonamido)ethyl)piperazine-1-carboxylate 33 (0.135 g, 0.245 mmol) as starting material to afford the desired 3-(benzylamino)-4-(cyclohexylamino)-N-(2-(piperazin-1-yl)ethyl) benzenesulfonamide hydrochloride 39 (0.110 g, 0.216 mmol). (Yield: 88%). The reported NMR spectrum is that of the free base of 39.

$^1$H NMR (400 MHz, DMSO-d$_6$) δ 1.15-1.29 (m, 4H), 1.31-1.45 (m, 2H), 1.59-1.68 (m, 1H), 1.70-1.80 (m, 2H), 1.95-2.04 (m, 2H), 2.10-2.21 (m, 6H), 2.56 (t, J=7.1 Hz, 2H), 2.61 (t, J=4.8 Hz, 4H), 3.33-3.39 (m, 1H), 4.32 (d, J=5.3 Hz, 2H), 5.13 (d, J=7.2 Hz, 1H), 5.69 (t, J=5.7 Hz, 1H), 6.54 (d, J=8.4 Hz, 1H), 6.72 (d, J=2.1 Hz, 1H), 6.74-6.80 (m, 1H), 6.97 (dd, J=8.3, 2.1 Hz, 1H), 7.20-7.29 (m, 1H), 7.30-7.40 (m, 4H).

$^{13}$C NMR (101 MHz, DMSO-d6) δ 24.68, 25.57, 32.46, 39.73, 45.38, 46.88, 50.86, 53.89, 57.34, 107.48, 117.20, 125.76, 126.76, 127.33, 128.28, 134.49, 138.33, 139.40.

t$_R$ 1.44 min, MS (ESI) m/z 472 [M+H] 100(%)

4-(cyclohexylamino)-N-(2-(dimethylamino)ethyl)-3-((pyridin-4-ylmethyl)amino)benzenesulfonamide (40)

By following General Procedure D, the reaction mixture was prepared using 3-amino-4-(cyclohexylamino)-N-(2-(dimethylamino)ethyl)benzenesulfonamide 20 (0.293 g, 0.861 mmol, 1 equiv.), 4-(bromomethyl)pyridine hydrobromide (0.218 g, 0.861 mmol, 1 equiv.) and potassium carbonate (0.119 g, 0.861 mmol, 1 equiv.). This mixture was allowed to stir for 30 minutes at room temperature. The mixture was diluted with water and washed with EtOAc. The aqueous layer was concentrated, lyophilised and purified further using reverse phase flash chromatography (Water/MeOH) to afford the desired 4-(cyclohexylamino)-N-(2-(dimethylamino)ethyl)-3-((pyridin-4-ylmethyl)amino)benzenesulfonamide 40 (0.170 g, 0.394 mmol) (Yield: 45.8%)

$^1$H NMR (400 MHz, Methanol-d$_4$) δ 1.23-1.35 (m, 3H), 1.37-1.50 (m, 2H), 1.70 (dt, J=12.8, 3.6 Hz, 1H), 1.81 (dt, J=13.3, 3.6 Hz, 2H), 2.02-2.10 (m, 2H), 3.19 (s, 6H), 3.34-3.39 (m, 1H), 3.43 (t, J=6.2 Hz, 2H), 3.59 (t, J=6.3 Hz, 2H), 4.72 (s, 2H), 6.63 (d, J=9.1 Hz, 1H), 7.21-7.25 (m, 2H), 7.63-7.66 (m, 2H), 8.68-8.71 (m, 2H).

$^{13}$C NMR (101 MHz, Methanol-d$_4$) δ 26.30, 27.05, 34.08, 38.44, 51.70, 52.69, 64.96, 67.94, 109.97, 114.39, 121.01, 125.56, 129.35, 135.46, 138.05, 141.76, 151.35.

t$_R$ 1.35 min, MS (ESI) m/z 432 [M+H] (100%)

tert-butyl (2-((4-(cyclohexylamino)-3-((pyridin-4-ylmethyl)amino)phenyl)sulfonamido)ethyl)(methyl) carbamate (41)

By following General Procedure D, the reaction mixture was prepared using tert-butyl (2-((3-amino-4-(cyclohexylamino)phenyl)sulfonamido)ethyl)(methyl)carbamate 21 (0.250 g, 0.586 mmol, 1 equiv.), 4-(bromomethyl)pyridine hydrobromide (0.148 g, 0.586 mmol, 1 equiv.) and potassium carbonate (0.081 g, 0.586 mmol, 1 equiv.). This mixture was allowed to stir for 40 minutes at 40° C. The mixture was diluted with water and washed with EtOAc. The aqueous layer was concentrated and purified further using normal phase flash chromatography (Heptane/Ethyl acetate) to afford the desired tert-butyl (2-((4-(cyclohexylamino)-3-((pyridin-4-ylmethyl)amino)phenyl)sulfonamido)ethyl)(methyl)carbamate 41 (0.070 g, 0.135 mmol) (Yield: 23.1%). The compound was immediately introduced in the next step.

tert-butyl (2-((4-(cyclohexylamino)-3-((pyridin-4-ylmethyl)amino)phenyl)sulfonamido)ethyl)carbamate (42)

By following General Procedure D, the reaction mixture was prepared using tert-butyl (2-((3-amino-4-(cyclohexylamino)phenyl)sulfonamido)ethyl)carbamate 22 (0.400 g, 0.970 mmol, 1 equiv.), 4-(bromomethyl)pyridine hydrobromide (0.490 g, 1.939 mmol, 2 equiv.) and potassium carbonate (0.402 g, 2.91 mmol, 3 equiv.). This mixture was allowed to stir for 60 minutes at 40° C. The mixture was diluted with water and washed with EtOAc. The aqueous layer was concentrated and purified further using normal phase flash chromatography (Heptane/Ethyl acetate) to afford the desired tert-butyl (2-((4-(cyclohexylamino)-3-((pyridin-4-ylmethyl)amino)phenyl)sulfonamido)ethyl)carbamate 42 (0.200 g, 0.387 mmol) (Yield: 41.0%).

$^1$H NMR (400 MHz, Acetone-d$_6$) δ 1.27-1.36 (m, 3H), 1.40 (s, 9H), 1.43-1.51 (m, 2H), 1.63-1.72 (m, 1H), 1.74-1.83 (m, 2H), 2.12 (d, J=3.9 Hz, 2H), 2.79 (q, J=6.3 Hz, 2H), 3.08 (q, J=6.2 Hz, 2H), 3.38-3.51 (m, 1H), 4.46 (d, J=5.4 Hz, 2H), 4.57-4.66 (m, 1H), 4.93-5.06 (m, 1H), 5.92 (s, 1H), 6.03-6.12 (m, 1H), 6.72 (d, J=8.4 Hz, 1H), 6.92 (d, J=2.1 Hz, 1H), 7.20 (dd, J=8.3, 2.1 Hz, 1H), 7.38 (dd, J=4.7, 1.6 Hz, 2H), 8.47-8.59 (m, 2H).

$^{13}$C NMR (101 MHz, Acetone-d$_6$) δ 24.79, 25.76, 27.73, 32.88, 43.09, 46.67, 51.38, 78.00, 108.73, 109.76, 119.09, 122.44, 127.37, 134.81, 139.94, 148.69, 149.78, 155.96.

tert-butyl 4-(2-((4-(cyclohexylamino)-3-((pyridin-4-ylmethyl)amino)phenyl)sulfonamido)ethyl)piperazine-1-carboxylate (43)

By following General Procedure D, the reaction mixture was prepared using tert-butyl 4-(2-((3-amino-4-(cyclohexylamino)phenyl)sulfonamido)ethyl)piperazine-1-carboxylate 23 (0.400 g, 0.830 mmol, 1 equiv.), 4-(bromomethyl)pyridine hydrobromide (0.420 g, 1.661 mmol, 2 equiv.) and potassium carbonate (0.344 g, 2.491 mmol, 3 equiv.). This mixture was allowed to stir for 2 hours at 40° C. The mixture was diluted with water and washed with EtOAc. The aqueous layer was concentrated and purified further using normal phase flash chromatography (Heptane/Ethyl acetate) to afford the desired tert-butyl 4-(2-((4-(cyclohexylamino)-3-((pyridin-4-ylmethyl)amino)phenyl)sulfonamido)ethyl)piperazine-1-carboxylate 43 (0.160 g, 0.279 mmol) (Yield: 33.6%).

$^1$H NMR (400 MHz, DMSO-d6) δ 1.24 (s, 3H), 1.39 (s, 11H), 1.62-1.69 (m, 1H), 1.72-1.79 (m, 2H), 1.97-2.06 (m, 2H), 2.13 (t, J=5.0 Hz, 4H), 2.18 (t, J=6.8 Hz, 2H), 2.53-2.59 (m, 2H), 3.18-3.28 (m, 4H), 3.38 (s, 1H), 4.38 (d, J=5.5 Hz, 2H), 5.10 (d, J=7.2 Hz, 1H), 5.82 (t, J=5.7 Hz, 1H), 6.57 (d, J=8.5 Hz, 1H), 6.61 (d, J=2.1 Hz, 1H), 6.78 (t, J=5.8 Hz, 1H), 6.98 (dd, J=8.3, 2.1 Hz, 1H), 7.30-7.37 (m, 2H), 8.47-8.55 (m, 2H).

$^{13}$C NMR (101 MHz, Acetone-d$_6$) δ 25.73, 26.69, 28.62, 33.76, 40.60, 44.38, 47.46, 52.28, 53.29, 57.03, 79.53, 109.68, 110.56, 119.88, 123.32, 127.91, 135.61, 140.74, 149.65, 150.68, 154.97.

4-(cyclohexylamino)-N-(2-(4-methylpiperazin-1-yl)ethyl)-3-((pyridin-4-ylmethyl)amino)benzenesulfonamide (44)

By following General Procedure D, the reaction mixture was prepared using 3-amino-4-(cyclohexylamino)-N-(2-(4-methylpiperazin-1-yl)ethyl)benzenesulfonamide 24 (0.300 g, 0.758 mmol, 1 equiv.), 4-(bromomethyl)pyridine hydrobromide (0.0.192 g, 0.758 mmol, 1 equiv.) and potassium carbonate (0.105 g, 0.758 mmol, 1 equiv.). This mixture was allowed to stir for 15 minutes at room temperature. The mixture was diluted with water and washed with EtOAc. The aqueous layer was concentrated, lyophilisated and purified further using reverse phase flash chromatography (Water/MeOH) to afford the desired 4-(cyclohexylamino)-N-(2-(4-methylpiperazin-1-yl)ethyl)-3-((pyridin-4-ylmethyl)amino)benzenesulfonamide 44 (0.170 g, 0.349 mmol) (Yield: 46.1%)

$^1$H NMR (400 MHz, Methanol-$d_4$) δ 1.22-1.34 (m, 3H), 1.36-1.50 (m, 2H), 1.69 (dt, J=12.8, 3.8 Hz, 1H), 1.80 (dt, J=13.2, 3.7 Hz, 2H), 1.99-2.10 (m, 2H), 2.52 (t, J=6.0 Hz, 2H), 2.58-2.67 (m, 2H), 2.71-2.79 (m, 2H), 3.00 (t, J=6.0 Hz, 2H), 3.05 (s, 3H), 3.34-3.40 (m, 3H), 3.55-3.64 (m, 2H), 4.74 (s, 2H), 6.63 (d, J=8.5 Hz, 1H), 7.21 (dd, J=8.4, 2.3 Hz, 1H), 7.29 (d, J=2.2 Hz, 1H), 7.69-7.71 (m, 2H), 8.70-8.73 (m, 2H).

$^{13}$C NMR (101 MHz, Methanol-$d_4$) δ 26.32, 27.06, 34.12, 41.03, 46.96, 52.71, 56.22, 61.67, 109.75, 114.37, 120.85, 127.09, 129.54, 135.48, 137.79, 141.25, 151.31.

$t_R$ 1.35 min, MS (ESI) m/z 487 [M+H] (100%)

4-(cyclohexylamino)-N-(2-morpholinoethyl)-3-((pyridin-4-ylmethyl)amino)benzenesulfonamide (45)

By following General Procedure D, the reaction mixture was prepared using 3-amino-4-(cyclohexylamino)-N-(2-morpholinoethyl)benzenesulfonamide 25 (0.200 g, 0.523 mmol, 1 equiv.), 4-(bromomethyl)pyridine hydrobromide (0.246 g, 1.046 mmol, 2 equiv.) and potassium carbonate (0.217 g, 1.569 mmol, 3 equiv.). This mixture was allowed to stir for 2 hours at 60° C. The mixture was diluted with EtOAc and washed with water. The organic layer was dried using anhydrous sodium sulfate, concentrated and purified further using normal phase flash chromatography on silica gel (Heptanes/EtOAc/MeOH) to afford the desired 4-(cyclohexylamino)-N-(2-morpholinoethyl)-3-((pyridin-4-ylmethyl)amino)benzenesulfonamide 45 (0.065 g, 0.137 mmol) (Yield: 26.3%)

$^1$H NMR (400 MHz, Methanol-$d_4$) δ 1.24-1.36 (m, 3H), 1.39-1.52 (m, 2H), 1.71 (dt, J=13.1, 3.6 Hz, 1H), 1.82 (dt, J=13.2, 3.7 Hz, 2H), 2.06-2.14 (m, 2H), 2.25-2.30 (m, 6H), 2.73 (t, J=6.5 Hz, 2H), 3.39 (tt, J=10.4, 3.7 Hz, 1H), 3.59 (t, J=4.7 Hz, 4H), 4.46 (s, 2H), 6.66 (d, J=8.5 Hz, 1H), 6.78 (d, J=2.1 Hz, 1H), 7.19 (dd, J=8.4, 2.1 Hz, 1H), 7.41-7.44 (m, 2H), 8.43-8.46 (m, 2H).

$^{13}$C NMR (101 MHz, Methanol-$d_4$) δ 26.28, 27.11, 34.13, 40.59, 47.50, 52.81, 54.44, 58.28, 67.60, 109.80, 110.24, 120.25, 124.15, 126.87, 135.74, 141.26, 150.13, 152.08.

$t_R$ 1.34 min, MS (ESI) m/z 474 [M+H] (100%)

4-(cyclohexylamino)-N-(2-methoxyethyl)-3-((pyridin-4-ylmethyl)amino)benzenesulfonamide (46)

By following General Procedure D, the reaction mixture was prepared using 3-amino-4-(cyclohexylamino)-N-(2-methoxyethyl)benzenesulfonamide 26 (0.400 g, 1.222 mmol, 1 equiv.), 4-(bromomethyl)pyridine hydrobromide (0.618 g, 2.443 mmol, 2 equiv.) and potassium carbonate (0.506 g, 3.66 mmol, 3 equiv.). This mixture was allowed to stir for 4 hours at 60° C. The mixture was diluted with EtOAc and washed with water. The organic layer was dried using anhydrous sodium sulfate, concentrated and purified further using normal phase flash chromatography on silica gel (Heptanes/EtOAc) to afford the desired 4-(cyclohexylamino)-N-(2-methoxyethyl)-3-((pyridin-4-ylmethyl)amino)benzenesulfonamide 46 (0.212 g, 0.507 mmol) (Yield: 41.5%)

$^1$H NMR (400 MHz, DMSO-$d_6$) δ 1.18-1.36 (m, 3H), 1.36-1.51 (m, 2H), 1.63-1.73 (m, 1H), 1.73-1.85 (m, 2H), 1.98-2.10 (m, 2H), 2.64 (q, J=6.0 Hz, 2H), 3.19 (s, 3H), 3.22 (t, J=6.0 Hz, 2H), 3.39 (ddt, J=8.9, 6.0, 3.1 Hz, 1H), 4.45 (s, 2H), 5.14 (s, 1H), 5.89 (s, 1H), 6.61 (d, J=8.4 Hz, 1H), 6.65 (d, J=2.1 Hz, 1H), 7.00-7.09 (m, 2H), 7.40-7.50 (m, 2H), 8.50-8.66 (m, 2H).

$^{13}$C NMR (101 MHz, DMSO-$d_6$) δ 25.11, 26.05, 32.97, 42.41, 46.25, 51.38, 58.30, 70.96, 108.15, 108.28, 118.08, 123.09, 126.62, 134.50, 139.04, 149.18, 150.64.

$t_R$ 1.37 min, MS (ESI) m/z 419 [M+H] (100%)

4-(cyclohexylamino)-N-(2-(methylamino)ethyl)-3-((pyridin-4-ylmethyl)amino)benzenesulfonamide Hydrochloride (47)

By following General Procedure E using tert-butyl (2-((4-(cyclohexylamino)-3-((pyridin-4-ylmethyl)amino)phenyl)sulfonamido)ethyl)(methyl)carbamate 41 (0.070 g, 0.135 mmol) as starting material to afford the desired 4-(cyclohexylamino)-N-(2-(methylamino)ethyl)-3-((pyridin-4-ylmethyl)amino)benzenesulfonamide hydrochloride 47 (0.059 g, 0.130 mmol). (Yield: 96%). The reported NMR spectrum is that of the free base of 47.

$^1$H NMR (400 MHz, DMSO-$d_6$) δ 1.21-1.35 (m, 3H), 1.38-1.51 (m, 2H), 1.65-1.74 (m, 1H), 1.77-1.86 (m, 2H), 2.01-2.10 (m, 2H), 2.19 (s, 3H), 2.39 (t, J=6.4 Hz, 2H), 2.54-2.56 (m, 2H), 3.35-3.46 (m, 1H), 4.43 (d, J=5.4 Hz, 2H), 5.18 (d, J=7.1 Hz, 1H), 5.90 (t, J=5.6 Hz, 1H), 6.62 (d, J=8.5 Hz, 1H), 6.65 (d, J=2.1 Hz, 1H), 7.03 (dd, J=8.4, 2.1 Hz, 1H), 7.29-7.48 (m, 2H), 8.49-8.63 (m, 2H).

$^{13}$C NMR (101 MHz, DMSO-$d_6$) δ 24.64, 25.56, 32.46, 35.50, 41.86, 45.70, 50.26, 50.84, 107.50, 107.68, 117.48, 122.29, 125.96, 134.04, 138.42, 148.82, 149.52.

$t_R$ 1.19 min, MS (ESI) m/z 418 [M+H] (100%)

N-(2-aminoethyl)-4-(cyclohexylamino)-3-((pyridin-4-ylmethyl)amino)benzenesulfonamide Hydrochloride (48)

By following General Procedure E using tert-butyl (2-((4-(cyclohexylamino)-3-((pyridin-4-ylmethyl)amino)phenyl)sulfonamido)ethyl)carbamate 42 (0.050 g, 0.124 mmol) as starting material to afford the desired 4 N-(2-aminoethyl)-4-(cyclohexylamino)-3-((pyridin-4-ylmethyl)amino)benzenesulfonamide hydrochloride 48 (0.039 g, 0.089 mmol). (Yield: 71.1%). The reported NMR spectrum is that of the free base of 48.

$^1$H NMR (400 MHz, Methanol-$d_4$) δ 1.22-1.39 (m, 3H), 1.40-1.54 (m, 2H), 1.68-1.79 (m, 1H), 1.80-1.88 (m, 2H), 2.06-2.16 (m, 2H), 2.84 (t, J=6.7 Hz, 2H), 3.16 (t, J=6.7 Hz, 2H), 3.35-3.46 (m, 1H), 4.48 (s, 2H), 6.67 (d, J=8.4 Hz, 1H), 6.77 (d, J=2.1 Hz, 1H), 7.18 (dd, J=8.4, 2.1 Hz, 1H), 7.35-7.55 (m, 2H), 8.29-8.51 (m, 2H).

$^{13}$C NMR (101 MHz, Methanol-$d_4$) δ 26.26, 27.10, 34.13, 44.24, 47.52, 51.57, 52.80, 109.76, 110.22, 120.20, 124.10, 127.31, 135.77, 141.24, 150.09, 150.11, 152.10.

$t_R$ 1.24 min, MS (ESI) m/z 404 [M+H] (100%)

4-(cyclohexylamino)-N-(2-(piperazin-1-yl)ethyl)-3-((pyridin-4-ylmethyl)amino)benzenesulfonamide Hydrochloride (49)

By following General Procedure E using tert-butyl 4-(2-((4-(cyclohexylamino)-3-((pyridin-4-ylmethyl)amino)phenyl)sulfonamido)ethyl)piperazine-1-carboxylate 43 (0.150 g, 0.262 mmol) as starting material to afford the desired 4-(cyclohexylamino)-N-(2-(piperazin-1-yl)ethyl)-3-((pyridin-4-ylmethyl)amino)benzenesulfonamide hydrochloride 49 (0.075 g, 0.147 mmol). The reported NMR spectrum is that of the free base of 49.

$^1$H NMR (400 MHz, DMSO-$d_6$) δ 1.20-1.54 (m, 6H), 1.66-1.74 (m, 1H), 1.76-1.86 (m, 2H), 2.01-2.11 (m, 2H), 2.13-2.26 (m, 6H), 2.57-2.61 (m, 2H), 2.66 (t, J=4.7 Hz, 4H), 3.22-3.33 (m, 1H), 4.43 (d, J=5.5 Hz, 2H), 5.18 (d, J=7.2 Hz, 1H), 5.90 (t, J=5.7 Hz, 1H), 6.62 (d, J=8.5 Hz, 1H), 6.65 (d, J=2.1 Hz, 1H), 6.81 (t, J=5.5 Hz, 1H), 7.03 (dd, J=8.3, 2.1 Hz, 1H), 7.36-7.44 (m, 2H), 8.54-8.59 (m, 2H).

$^{13}$C NMR (101 MHz, DMSO-$d_6$) δ 24.63, 25.55, 32.45, 45.41, 45.66, 50.84, 53.94, 57.31, 107.51, 107.72, 117.52, 122.26, 125.82, 134.03, 138.42, 148.82, 149.52.

$t_R$ 1.12 min, MS (ESI) m/z 473 [M+H] (100%)

3. Activity of Specific Compounds of the Invention

The IC50 values for the individual compounds of the invention were determined in the neuroblastoma, IMR-32 cell line. In brief, IMR-32 cells were subjected to 10 μM erastin, the latter compound is known to induce ferroptosis. A concentration gradient (ranging from 1 nM to 1 μM) of the compounds was applied to the cells. These experiments were performed in a 96-well format (in triplicate), and cell death was analyzed in a fluorescent plate reader by use of a fluorescent cell death dye (1.5 μM Sytox Green). The IC50 values depicted in Table 1 are the concentration values for the individual compounds which are able to overcome ferroptosis.

The introduction of a cyclic or aliphatic amine at $E_1$ increased the kinetic solubility of this type of molecule significantly when compared to our earlier published results. [16] (Table 1) The introduction of a benzylic moiety at $E_2$ was well tolerated and improved potency in most cases. Compounds 35-39 for example, all of which contain a benzyl moiety in $E_2$, displayed a more potent inhibition of erastin-induced ferroptosis than their corresponding analogues which possess a primary amine or piridinylic moiety at this position. This potentiating effect was not observed as significantly when a pryidinylic group was introduced at the same position. A similar trend was observed in our previously published work. [16]

For example compound 35 has an $IC_{50}$-value of 24 nM combined with a solubility range of 50-100 μM. Even more remarkable is the fact that molecules 37-39 exhibit even lower $IC_{50}$-values combined with an excellent kinetic solubility (>200 μM). This increase in solubility while preserving the improved potency when compared to Fer-1 is a very promising feature of these compounds. The four most promising molecules (35, 37-39) were thus selected for further assessment and their in vitro ADME-parameters were defined.

TABLE 1

Synthesized fer-1 analogues and their antiferroptotic activity in response to erastin-induced ferroptosis in IMR-32 Neuroblastoma cells.

| Compound | $E_1$ or $E_3$ | $E_2$ | $IC_{50}$ (nM) | Solubility (μM)$^a$ |
|---|---|---|---|---|
| 1 (Fer-1) | / | —H | 33 | >200 |
| 20 | —N(Me)$_2$ | —H | 160 | >200 |
| 24 | N-Methylpiperazine | —H | 236 | >200 |
| 25 | Morpholine | —H | 448 | >200 |
| 26 | —OCH$_3$ | —H | 492 | >200 |
| 27 | —NH(Me) | —H | 214 | >200 |
| 28 | —NH$_2$ | —H | 306 | >200 |
| 29 | Piperazine | —H | 296 | >200 |
| 30 | —N(Me)$_2$ | Benzyl | 554 | >200 |
| 34 | N-Methylpiperazine | Benzyl | 1072 | >200 |
| 35 | Morpholine | Benzyl | 24 | 50-100 |
| 36 | —OCH$_3$ | Benzyl | 22 | 25-50 |
| 37 | —NH(Me) | Benzyl | 3 | >200 |
| 38 | —NH$_2$ | Benzyl | 12 | >200 |
| 39 | Piperazine | Benzyl | 10 | >200 |
| 40 | —N(Me)$_2$ | Pyridinyl | 1560 | >200 |
| 44 | N-Methylpiperazine | Pyridinyl | 1520 | >200 |
| 45 | Morpholine | Pyridinyl | 191 | >200 |
| 46 | —OCH$_3$ | Pyridinyl | 97 | >200 |
| 47 | —NH(Me) | Pyridinyl | 157 | >200 |
| 48 | —NH$_2$ | Pyridinyl | 112 | 100-200 |
| 49 | Piperazine | Pyridinyl | 442 | >200 |

$^a$ Final test compound concentration range between 3.125 μM and 200 μM [4 μM DMSO solution in 196 μM buffer solution (10 mM PBS pH 7.4)].
Reported $IC_{50}$ values are calculated from measurements in triplicate.

4. ADME Assays

The determination of both the microsomal and plasma stability of 35, 37-39 revealed a remarkable improvement in stability when compared to Fer-1 which is unstable under nearly all conditions. (Table 2 and Table 3) However, significant intraspecies differences between the four lead molecules were observed. Compounds 38 and 39 more specifically, showed a microsomal half-life ($t_{1/2}$) of multiple hours across all species. Compound 39 has an impressive $t_{1/2}$ when incubated with both human and rat microsomes ($t_{1/2}$=20.5 h and $t_{1/2}$=16.5 h respectively) but was found to be relatively less stable when incubated with murine microsomes ($t_{1/2}$=3.46 h). In contrast, compound 38 has a microsomal $t_{1/2}$ greater than 10 hours under both human ($t_{1/2}$=17.7 h) and murine ($t_{1/2}$=13 h) conditions but was microsomally less stable when incubated with rat microsomes ($t_{1/2}$=2.05 h).

TABLE 2

Solubility, microsomal stability and plasma stability of compounds 1, 35, 37-39.

| Compound | Microsomal stability ($t_{1/2}$) (h) [a] | | | Plasma stability (% recovery after 6 h) [b] | | |
|---|---|---|---|---|---|---|
| | Human | Rat | Mouse | Human | Rat | Mouse |
| 1 | 0.109 ± 0.003 | 0 | 0 | 47.3 | 1.1 | 0 |
| 35 | 0.98 ± 0.35 | 0.173 ± 0.007 | 0.051 ± 0.002 | 100 | 100 | 100 |
| 37 | 13.21 ± 4.10 | 0.35 ± 0.01 | 0.45 ± 0.02 | 90.3 | 65.8 | 100 |
| 38 | 17.71 ± 2.04 | 2.05 ± 0.21 | 13.00 ± 4.15 | 100 | 100 | 100 |
| 39 | 20.53 ± 5.49 | 16.48 ± 4.66 | 3.46 ± 1.37 | 84.2 | 85.8 | 100 |

[a] Metabolism by microsomes (CYP450 and other NADP-dependent enzymes) was monitored and expressed as half-life (h).
[b] Percentage of remaining parent compound.

Intrinsic Clearance ($Cl_{int}$) Calculations

By using the measured microsomal in vitro $t_{1/2}$, a calculated value for the intrinsic clearance $Cl_{int}$ can be determined. This value states the measure in which a drug that is not bound to plasma proteins is irreversibly removed from the body by the liver. This value is expressed in mL/min/kg which can be interpreted as the volume of blood in mL that is cleared of a drug per minute per kilogram of body weight. The $CL_{int}$ is less sensitive to used variables in ADME assays since the amount of microsomal protein and the volume of the incubation are all taken into account. (Sohlenius-Sternbeck et al., Xenobiotica, 2012, 42, 841-853)

$$CL_{int} = \frac{\ln 2}{t_{1/2}} \times \frac{\text{mL incubation}}{\text{mg protein}} \times \frac{\text{mg microsomal protein}}{\text{g liver}} \times \frac{\text{g liver}}{\text{kg body weight}}$$

TABLE 3

Calculated Intrinsic Clearance in vitro of compounds 35, 37-39. Table of standard physiological and in vitro scaling factors

| Parameter | Mouse | Rat | Human |
|---|---|---|---|
| Liver weight (g/kg) | 60 | 40 | 24 |
| Standard Body Weight (kg) | 0.025 | 0.25 | 70 |
| Microsomal Protein Yield (mg/g liver) | 45 | 61 | 40 |

| | Calculated Intrinsic Clearance in vitro ($Cl_{int}$) (mL/min/kg) | | |
|---|---|---|---|
| Compound | Human | Rat | Mouse |
| 35 | 22.6 ± 8.1 | 325.9 ± 13.2 | 1223.2 ± 48.0 |
| 37 | 1.7 ± 0.5 | 161.1 ± 4.6 | 138.6 ± 6.2 |
| 38 | 1.3 ± 0.1 | 27.4 ± 2.7 | 4.8 ± 1.5 |
| 39 | 1.1 ± 0.3 | 3.4 ± 1.0 | 18.0 ± 7.1 |

The $Cl_{int\ is}$ calculated using the measured microsomal $t_{1/2}$ and takes into account several experimental variables such as the protein concentration and the volume of incubation.

5. In Vivo Pharmacokinetics

In order to estimate how these in vitro ADME parameters correlate to an in vivo setting, compound 39 was selected for a single intravenous (iv) administration to three male Wistar rats at a dose of 5 mg/kg. Blood samples were obtained at various time points. (0.083, 0.25, 0.5, 1, 2, 4, and 24 h) The concentration of 39 was determined using UPLC analysis coupled with tandem quadrupole mass spectrometry. (See SI for additional information) Interestingly, plasma concentrations of 39 remained below the detection limit (<53.1 ng/mL) in nearly all samples. Only in 1 sample a concentration of 19.6 μL/mL was determined 5 minutes after dosing. These findings suggest that 39 is rapidly removed from the bloodstream and redistributed into various tissues, as can be expected for lipophilic basic compounds.

To assess the extent of tissue distribution of compound 39, various organs (liver, kidney and lungs) of all three rats were collected on ice at necropsy 24 hours after administration before being homogenized and analyzed. (Table 4) Significant concentrations of compound 39 were found in all analyzed tissues, which further solidifies our earlier findings considering tissue redistribution. Since the tissue concentration of compound 39 was determined 24 hours after iv dosage, these results also confirm the increase in stability of compound 39 when compared to Fer-1 which is unstable in in vivo conditions.

TABLE 4

Tissue distribution profile of compound 39 in various organs.

| | Tissue distribution profile of compound 39 (mg/kg organ, after 24 h) | | |
|---|---|---|---|
| | Liver | Kidney | Lung |
| Rat 1 | 0.23 | 0.20 | 0.19[a] |
| Rat 2 | 0.22 | 0.35 | 0.48 |
| Rat 3 | 0.15 | 0.38 | 0.53 |

Each rat received an iv dose at 5 mg/kg and the internal organs were collected at narcopsy at 24 h. The organs were homogenized and further processed by protein precipitation (n=3) and centrifugation. Analysis of the samples was conducted by LC-MS.
[a] For this measurement only two samples of organ homogenate were processed (n=2).

6. Pharmacokinetic Properties of Selected Compounds

Analysis of the pharmacokinetic properties of UAMC-3203 (compound 39 in Table 1), -3206 (compound 38 in Table 1) and -3234 (compound 37 in Table 1) upon single-dose iv injection in mice revealed almost undetectable levels in blood (FIG. 4). The tissue distribution profile 2 h after injection revealed a superior profile of UAMC-3203 compared to -3206 and the benchmark Fer-1. The detected levels of UAMC-3203 vary between 3-60 ng/mg tissue depending on the organ, which is up to 2-fold lower or 6-fold higher than the dose injected. Importantly, compound UAMC-3203, but not UAMC-3206, seems to cross the blood-brain barrier. The tissue distribution profile 24 h after injection revealed an overall drop in the levels of all compounds. UAMC-3234 was not detected in any organ, UAMC-3206 was detected in very low levels, UAMC-3203 and to a lesser extent Fer-1 were still present in range of 2- to 100-fold less than the dose injected.

7. Compounds of the Invention Protect Against Acute Iron Poisoning

We identified acute iron poisoning as a novel experimental model for in rhabdomyolysis-induced kidney failure. Three different selected compounds (37, 38 and 39—see Table 1 for structures) were clearly found to be more effective in reducing the plasma lactate dehydrogenase (LDH) and creatine kinase levels than the benchmark Ferrostatin-1 or Liproxtatin-1, both in a prophylactic setting (see FIG. 5A) as in a therapeutic setting (see FIG. 5B).

8. Compounds of the Invention Improve the Multiple Sclerosis Pathology in a Murine Model Experimental autoimmune encephalomyelitis (EAE) is an experimental mouse for multiple sclerosis. Compound 39 is a compound that efficiently crosses the blood brain barrier (see FIG. 4). Exploring the therapeutic efficacy of compound 39 in EAE revealed that compound 39, but not the benchmark Liproxtatin-1, improved the clinical disease scores during EAE pathology (see FIG. 6).

9. Further In Vivo Uses of Representative Compounds of the Invention

Compounds of the invention are tested in ferroptosis-driven liver damage. In particular, ferroptotic hepatotoxicity is induced by diquat (Higuchi M. et al (2011) *Biometals* 24(6): 1123-31, ML162 (Yang W S et al (2014) *Cell* 156 (1-2): 317-31), piperazine-Erastin (Yang W S et al (2014) *Cell* 156 (1-2): 317-31) or acetaminophen (van Swelm R P et al (2012) *Toxicol. Sci.* 129(1): 225-33). To illustrate their specificity, the compounds are also tested in necroptotic liver damage induced by concanavalin A (Zhou Y et al (2013) *Mediators Inflamm.* 2013: 706156) and apoptotic liver damage induced by TNF/Galactosamine (Liu J. et al (2013) *Oxid. Med. Cell Longev.* 2013: 305861). Liver damage is monitored by analyzing aspartate transaminase (AST) and alanine transaminase (ALT) levels in blood samples, but also cytosolic lactate dehydrogenase, mitochondrial DNA and lysosomal hexoaminidase as markers of cell death. This chemical-induced liver damage approach allows us to pinpoint quickly the most promising lead ferrostatin analogue. In a parallel genetic approach, we want to use tamoxifen-inducible GPX4 deficient mice that develop ferroptosis-driven acute renal failure (Friedmann Angeli J P et al (2014) *Nat Cell Biol.* 16(12):1180-91) to validate lead ferrostatin analogues. The most effective compound is subsequently validated in ischemia-reperfusion related pathologies such as cerebral or cardiac infarction, kidney IR and different models of septic shock (TNF-, LPS- and cecal ligation and puncture-induced shock; expertize in house). In addition, we are analyzing the role of iron-catalyzed necrosis in a clinical relevant setting vis-a-vis iron-storage disorders. Therefore, we are studying the role of iron-catalyzed necrosis in primary skin fibroblasts derived from patients with specific iron-storage disorders. We focus on cells derived from Friedreich ataxia patients with defects in the frataxin (FXN) gene because these cells were previously shown to be more sensitive for iron-catalyzed oxidative stress-induced cell death (Wong A et al (1999) *Hum Mol. Genet.* 8(3):425-30).

Materials and Methods

1. In Vitro ADME Experiments 1.1. Protocols 1.1.1. Kinetic Solubility

A turbidimetric method was used. First a series of DMSO compound stock solutions was prepared (0.15-5 mM). An aliquot of 4 μL stock solution was added to 196 μL PBS buffer (pH 7.4). A series of concentrations were prepared (3.13-200 μM), including a blank on a microtiter plate. (2% DMSO-D6) The microtiter plate was shaken for 10 seconds and incubated for 2 hours at 37° C. When there was no turbidity measured at a given concentration the sample was assumed to be dissolved.

1.1.2. Plasma Stability

5 μl of a 10 mM stock solution of the compound in DMSO was added to 995 μl of plasma to obtain a 50 μM final solution. The mixture was gently shaken for 6 h at 37° C. Aliquots of 100 μl were taken at various time points (0, 0.5 h, 1 h, 2 h, 3 h and 6 h) and diluted with 400 μl of cold methanol (stored at 4° C.). The suspension was centrifuged at 14000 rpm for 5 min. 50 μl of the supernatant was diluted with 950 μl of methanol and analysed with LC/MS/MS. The samples were analysed in triplicate. The experiment was done in duplicate. A standard curve of six points was made to fit the measured concentrations. Enalapril maleate was used as a control in mice, rats, and in human.

1.1.3. Metabolic Stability

Liver microsomes (20 mg protein/ml), NADPH regenerating system solutions A & B and 5 mM stock compound solution (100% DMSO) are prepared. The reaction mixture finally contains 713 μL purified water, 200 μL 0.5 M potassium phosphate pH 7.4, 50 μL NADPH regenerating system solution A (BD Biosciences Cat. No. 451220), 10 μL NADPH regenerating system solution B (BD Biosciences Cat. No. 451200) and 2 μL of the compound stock solution (10 μM final concentration). The reaction mixture is warmed to 37° C. for 5 minutes in a water bath and the reaction is initiated by addition of 25 μL of liver microsomes (0.5 mg protein/ml final concentration). At different time points (0 min-15 min-30 min-60 min-120 min-240 min-360 min-24 h), 20 μL is withdrawn and 80 μL cold acetonitrile is added on ice for 10 minutes. Then the mixtures are centrifuged at 13 000 rpm for 5 min at 4° C. The supernatant is further diluted in 90% water/MeCN (1/25) to fall within the range of the LC/MS/MS analysis. At each time point, the compound is analysed using LC/MS/MS with the same UPLC system as described above. A standard curve of six points was made to fit the measured concentrations. Verapamil was used as a positive control.

1.1.4. Data Processing and Linear Regression

All obtained readouts were processed using Microsoft Excel. In order to determine the microsomal half-life $t_{1/2}$ of the compounds, the rate constant k was determined by plotting the exponential decay graphs using GraFit. Microsomal $t_{1/2}$ was determined using the following formula:

$$t_{\frac{1}{2}} = \frac{\ln(2)}{k}$$

2. In Vivo Pharmacokinetics and Tissue Redistribution 2.1. Animals

Male Wistar rats (BW~250 g; Janvier France) were housed individually and randomly allocated to groups of 3 animals each based on body weight. The animals were fasted overnight until 4 hours after dosing. Drinking water remained available ad libitum.

2.2. Test Substance Formulation

The test compound were kept at 4° C. until formulation. The compound was formulated in PEG200 at 10 mg/ml. The test formulation was prepared by LMPH and stored at room temperature.

2.3. Blood and Tissue Sampling Procedure and Sample Processing

Blood was collected from sublingual vein using capillary tubes under isoflurane anaesthesia. The blood was dropped (15 µL) on Whatman® FTA® DMPK B cards, dried at room temperature for at least 2 hours and further processed for analysis. A 6 mm disk was punched from the blood spot center, extracted in 75:25 ACN:H2O containing tolbutamide as internal standard (IS). These tubes were vortexed and put in a sonication bath for 10 minutes. The extracts were centrifuged briefly and 50 µL of the supernatant was transferred to a 96-well LC-MS sample plate and diluted with 305 µL solvent. The optimal DBS protocol (FTA DMPK-A or B card, extraction solvent) was determined in a preliminary experiment.

Tissues (liver, kidneys and lungs) were collected on ice at necropsy at 24 h (after prior exsanguination), homogenized using a gentle MACS™ Dissociator and stored at −80° C. until analysis. The tissue samples for LC-MS were further processed by protein precipitation (n=3) by diluting 20 µL of the homogenate with 80 µL ACN containing IS (tolbutamide). After centrifugation, the supernatant was further diluted in the appropriate solvent.

REFERENCES (1) Wyllie, A. H.; Kerr, J. F. R.; Currie, A. R. *Cell Death: The Significance of Apoptosis;* 1980; Vol. 68.
(2) Taylor, R. C.; Cullen, S. P.; Martin, S. J. Apoptosis: Controlled Demolition at the Cellular Level. *Nat. Rev. Mol. Cell Biol.* 2008, 9 (3), 231-241.
(3) Vanden Berghe, T.; Hassannia, B.; Vandenabeele, P. An Outline of Necrosome Triggers. *Cell. Mol. Life Sci.* 2016, 73 (11-12), 2137-2152.
(4) Dondelinger, Y.; Hulpiau, P.; Saeys, Y.; Bertrand, M. J. M.; Vandenabeele, P. An Evolutionary Perspective on the Necroptotic Pathway. *Trends Cell Biol.* 2016, 26 (10), 721-732.
(5) Vanden Berghe, T.; Linkermann, A.; Jouan-Lanhouet, S.; Walczak, H.; Vandenabeele, P. Regulated Necrosis: The Expanding Network of Non-Apoptotic Cell Death Pathways. *Nat. Rev. Mol. Cell Biol.* 2014, 15 (2), 135-147.
(6) Conrad, M.; Angeli, J. P. F.; Vandenabeele, P.; Stockwell, B. R. Regulated Necrosis: Disease Relevance and Therapeutic Opportunities. *Nat. Rev. Drug Discov.* 2016.
(7) Dolma, S.; Lessnick, S. L.; Hahn, W. C.; Stockwell, B. R. Identification of Genotype-Selective Antitumor Agents Using Synthetic Lethal Chemical Screening in Engineered Human Tumor Cells. *Cancer Cell* 2003, 3 (3), 285-296.
(8) Yagoda, N.; von Rechenberg, M.; Zaganjor, E.; Bauer, A. J.; Yang, W. S.; Fridman, D. J.; Wolpaw, A. J.; Smukste, I.; Peltier, J. M.; Boniface, J. J.; Smith, R.; Lessnick, S. L.; Sahasrabudhe, S.; Stockwell, B. R. RAS-RAF-MEK-Dependent Oxidative Cell Death Involving Voltage-Dependent Anion Channels. *Nature* 2007, 447 (7146), 865-869.
(9) Dixon, S. J.; Lemberg, K. M.; Lamprecht, M. R.; Skouta, R.; Zaitsev, E. M.; Gleason, C. E.; Patel, D. N.; Bauer, A. J.; Cantley, A. M.; Yang, W. S.; Morrison, B.; Stockwell, B. R. Ferroptosis: An Iron-Dependent Form of Nonapoptotic Cell Death. *Cell* 2012, 149 (5), 1060-1072.
(10) Zilka, O.; Shah, R.; Li, B.; Friedmann Angeli, J. P.; Griesser, M.; Conrad, M.; Pratt, D. A. On the Mechanism of Cytoprotection by Ferrostatin-1 and Liproxstatin-1 and the Role of Lipid Peroxidation in Ferroptotic Cell Death. *ACS Cent. Sci.* 2017, acscentsci.7b00028.
(11) Dixon, S. J.; Lemberg, K. M.; Lamprecht, M. R.; Skouta, R.; Zaitsev, E. M.; Gleason, C. E.; Patel, D. N.; Bauer, A. J.; Cantley, A. M.; Yang, W. S.; Morrison III, B.; Stockwell, B. R. Ferroptosis: An Iron-Dependent Form of Nonapoptotic Cell Death. *Cell* 2012, 149 (5), 1060-1072.
(12) Cao, J. Y.; Dixon, S. J. Mechanisms of Ferroptosis. *Cell. Mol. Life Sci.* 2016, 73 (11-12), 2195-2209.
(13) Yang, W. S.; Sriramaratnam, R.; Welsch, M. E.; Shimada, K.; Skouta, R.; Viswanathan, V. S.; Cheah, J. H.; Clemons, P. A.; Shamji, A. F.; Clish, C. B.; Brown, L. M.; Girotti, A. W.; Cornish, V. W.; Schreiber, S. L.; Stockwell, B. R. Regulation of Ferroptotic Cancer Cell Death by GPX4. *Cell* 2014, 156 (1-2), 317-331.
(14) Seiler, A.; Schneider, M.; Förster, H.; Roth, S.; Wirth, E. K.; Culmsee, C.; Plesnila, N.; Kremmer, E.; Rådmark, O.; Wurst, W.; Bornkamm, G. W.; Schweizer, U.; Conrad, M. Glutathione Peroxidase 4 Senses and Translates Oxidative Stress into 12/15-Lipoxygenase Dependent- and AIF-Mediated Cell Death. *Cell Metab.* 2008, 8 (3), 237-248.
(15) Brigelius-Flohé, R.; Maiorino, M. Glutathione Peroxidases. *Biochim. Biophys. Acta-Gen. Subj.* 2013, 1830 (5), 3289-3303.
(16) Hofmans, S.; Berghe, T. Vanden; Devisscher, L.; Hassannia, B.; Lyssens, S.; Joossens, J.; Van Der Veken, P.; Vandenabeele, P.; Augustyns, K. Novel Ferroptosis Inhibitors with Improved Potency and ADME Properties. *J. Med. Chem.* 2016, 59 (5), 2041-2053.
(17) Angeli, J. P. F.; Shah, R.; Pratt, D. A.; Conrad, M. Ferroptosis Inhibition: Mechanisms and Opportunities. *Trends Pharmacol. Sci.* 2017, 38 (5), 489-498.
(18) Skouta, R.; Dixon, S. J.; Wang, J.; Dunn, D. E.; Orman, M.; Shimada, K.; Rosenberg, P. A.; Lo, D. C.; Weinberg, J. M.; Linkermann, A.; Stockwell, B. R. Ferrostatins Inhibit Oxidative Lipid Damage and Cell Death in Diverse Disease Models. *J Am Chem Soc* 2014, 136 (12), 4551-4556.
(19) Friedmann Angeli, J. P.; Schneider, M.; Proneth, B.; Tyurina, Y. Y.; Tyurin, V. a; Hammond, V. J.; Herbach, N.; Aichler, M.; Walch, A.; Eggenhofer, E.; Basavarajappa, D.; Rådmark, O.; Kobayashi, S.; Seibt, T.; Beck, H.; Neff, F.; Esposito, I.; Wanke, R.; Förster, H.; Yefremova, O.; Heinrichmeyer, M.; Bornkamm, G. W.; Geissler, E. K.; Thomas, S. B.; Stockwell, B. R.; O'Donnell, V. B.; Kagan, V. E.; Schick, J. a; Conrad, M. Inactivation of the Ferroptosis Regulator Gpx4 Triggers Acute Renal Failure in Mice. *Nat. Cell Biol.* 2014, 3 (August), 1-9.
(20) Yoo, S. E.; Chen, L.; Na, R.; Liu, Y.; Rios, C.; Van Remmen, H.; Richardson, A.; Ran, Q. Gpx4 Ablation in Adult Mice Results in a Lethal Phenotype Accompanied by Neuronal Loss in Brain. *Free Radic. Biol. Med.* 2012, 52 (9), 1820-1827.
(21) Chen, L.; Na, R.; Gu, M.; Richardson, A.; Ran, Q. Lipid Peroxidation up-Regulates BACE1 Expression in Vivo: A Possible Early Event of Amyloidogenesis in Alzheimer's Disease. *J. Neurochem.* 2008, 107 (1), 197-207.
(22) Sengupta, A.; Lichti, U.; Carlson, B.; Cataisson, C.; Ryscavage, A. O.; Mikulec, C.; Conrad, M.; Fischer, S. M.; Hatfield, D. L.; Yuspa, S. H. Targeted Disruption of Glutathione Peroxidase 4 in Mouse Skin Epithelial Cells Impairs Postnatal Hair Follicle Morphogenesis That Is Partially Rescued through Inhibition. *J. Invest. Dermatol.* 2013, 133 (7), 1731-1741.
(23) Wortmann, M.; Schneider, M.; Pircher, J.; Hellfritsch, J.; Aichler, M.; Vegi, N.; Kolle, P.; Kuhlencordt, P.; Walch, A.; Pohl, U.; Bornkamm, G. W.; Conrad, M.; Beck, H. Combined Deficiency in Glutathione Peroxidase 4 and Vitamin E Causes Multiorgan Thrombus Formation and Early Death in Mice. Circ. Res. 2013, 113 (4), 408-417.

(24) Ueta, T.; Inoue, T.; Furukawa, T.; Tamaki, Y.; Nakagawa, Y.; Imai, H.; Yanagi, Y. Glutathione Peroxidase 4 Is Required for Maturation of Photoreceptor Cells. *J. Biol. Chem.* 2012, 287 (10), 7675-7682.

(25) Linkermann, A.; Skouta, R.; Himmerkus, N.; Mulay, S. R.; Dewitz, C.; De Zen, F.; Prokai, A.; Zuchtriegel, G.; Krombach, F.; Welz, P.-S.; Weinlich, R.; Vanden Berghe, T.; Vandenabeele, P.; Pasparakis, M.; Bleich, M.; Weinberg, J. M.; Reichel, C. a; Brasen, J. H.; Kunzendorf, U.; Anders, H.-J.; Stockwell, B. R.; Green, D. R.; Krautwald, S. Synchronized Renal Tubular Cell Death Involves Ferroptosis. *Proc. Natl. Acad. Sci. U.S.A.* 2014, 111 (47), 16836-16841.

The invention claimed is:

1. A compound depicted in formula (I)

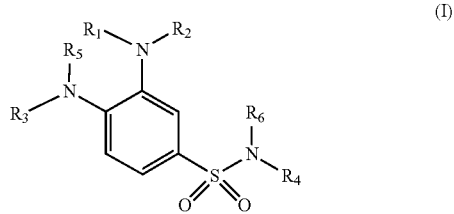

(I)

wherein
- R1 is selected from the group consisting of H and aryl-substituted C1-C4-alkyl;
- R2 is selected from the group consisting of H and aryl-substituted C1-C4-alkyl;
- R3 is selected from the group consisting of a C3-C12-cycloalkyl optionally substituted with one of more halogens, optionally replacing one or more carbons by heteroatoms in the cycloalkyl ring structure;
- R4 is selected from the group consisting of C1-C4-alkyl, wherein said C1-C4-alkyl is terminated with an R7 group wherein R7 is a C3-C10-heterocycle optionally substituted with one or more halogens;
- R5 is selected from the group consisting of H or C3-C12-cycloalkyl optionally substituted with one of more halogens, optionally replacing one or more carbons by heteroatoms in the cycloalkyl ring structure; and
- R6 is selected from the group consisting of H or a structure as defined in R4;

and pharmaceutically acceptable salts thereof, and individual enantiomers and diastereomers thereof.

2. A compound according to claim 1, wherein R1 or R2 is a pyridinyl-substituted C1-C4-alkyl.

3. A compound according to claim 1, selected from the group consisting of 3-amino-4-(cyclohexylamino)-N-(2-(4-methylpiperazin-1-yl)ethyl)benzenesulfonamide, 3-amino-4-(cyclohexylamino)-N-(2-morpholino-ethyl)benzenesulfonamide, 3-amino-4-(cyclohexylamino)-N-(2-(piperazin-1-yl)ethyl)-benzenesulfonamide, 3-(benzylamino)-4-(cyclohexylamino)-N-(2-(4-methylpiperazin-1-yl)ethyl) benzenesulfonamide, 4-(cyclohexylamino)-N-(2-(4-methylpiperazin-1-yl)ethyl)-3-((pyridin-4-ylmethyl)amino) benzenesulfonamide, 4-(cyclohexylamino)-N-(2-morpholinoethyl)-3-((pyridin-4-ylmethyl)amino) benzenesulfonamide, 4-(cyclohexylamino)-N-(2-(piperazin-1-yl)ethyl)-3-((pyridin-4-ylmethyl)amino) benzenesulfonamide hydrochloride, 3-(benzylamino)-4-(cyclohexylamino)-N-(2-morpholinoethyl) benzenesulfonamide and 3-(benzylamino)-4-(cyclohexylamino)-N-(2-(piperazin-1-yl)ethyl) benzenesulfonamide hydrochloride.

4. A medicament comprising a compound of claim 1 or a stereoisomer, a tautomer, an N-oxide, a hydrate, a solvate, or a salt thereof, particularly a pharmaceutically acceptable salt thereof, or a mixture of the same in an amount sufficient to inhibit ferroptosis and/or oxytosis in a subject.

5. A pharmaceutical composition comprising a compound according to claim 1, or a stereoisomer, a tautomer, an N-oxide, a hydrate, a solvate, or a salt thereof, particularly a pharmaceutically acceptable salt thereof, or a mixture of the same; and a pharmaceutically acceptable carrier or diluent.

6. A method of inhibiting ferroptosis and/or oxytosis in a subject comprising administering to the subject the pharmaceutical composition according to claim 5 so as to inhibit ferroptosis and/or oxytosis in the subject.

7. A method of treating a subject for a disease where an excess of ferroptosis and/or oxytosis occurs, wherein the disease is selected from stroke, myocardial infarction, diabetes, sepsis, the prevention of transplant rejection, neurodegenerative diseases including Alzheimer's Disease, Parkinson's Disease, Amyotrophic lateral sclerosis, Huntington's Disease, Dementia with Lewy bodies, Friedreich's ataxia and multiple sclerosis, the method comprising administering to the subject the pharmaceutical composition according to claim 5.

* * * * *